United States Patent [19]

Suhr et al.

[11] 4,264,605

[45] Apr. 28, 1981

[54] 1-BENZOYL-3-(ARYLOXY- OR ARYLTHIOPYRIDINYL) UREA COMPOUNDS

[75] Inventors: Robert G. Suhr, Greenfield; John L. Miesel, Indianapolis, both of Ind.

[73] Assignee: Eli Lilly and Company, Indianapolis, Ind.

[21] Appl. No.: 48,300

[22] Filed: Jun. 13, 1979

Related U.S. Application Data

[63] Continuation-in-part of Ser. No. 938,721, Aug. 31, 1978, abandoned.

[51] Int. Cl.³ .................... A01N 43/40; C07D 213/75
[52] U.S. Cl. ...................... 424/263; 546/292
[58] Field of Search .................... 546/292; 424/263

[56] References Cited

U.S. PATENT DOCUMENTS 3,748,356 7/1973 Wellings et al. ................. 260/553 E

FOREIGN PATENT DOCUMENTS 2748636 3/1978 Fed. Rep. of Germany ........... 546/292

*Primary Examiner*—Alan L. Rotman
*Attorney, Agent, or Firm*—Gerald V. Dahling; Kathleen R. S. Page; Arthur R. Whale

[57] ABSTRACT

The present invention is directed to 1-benzoyl-3-(aryloxy- or arylthio-pyridinyl)urea compounds useful as insecticides.

160 Claims, No Drawings

1-BENZOYL-3-(ARYLOXY- OR ARYLTHIOPYRIDINYL) UREA COMPOUNDS

CROSS-REFERENCE TO RELATED APPLICATION

This is a continuation-in-part of our copending application Ser. No. 938,721, filed Aug. 31, 1978 now abandoned.

SUMMARY OF THE INVENTION

More particularly the present invention is directed to novel compounds of the formula

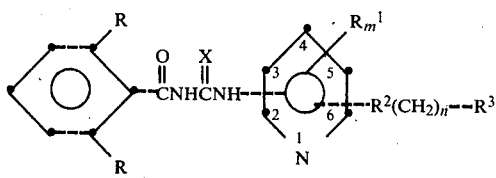

wherein each R is independently chloro, fluoro, methyl, or methoxy, with the proviso that when n is O, one R is chloro, and $R^3$ is 3-(trifluoromethyl)-phenyl or 2-chloro-5-(trifluoromethyl)phenyl, the other R can additionally represent hydrogen; X is oxygen or sulfur; $R^1$ is chloro, methyl, or ethyl;

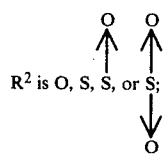

each of m and n is independently 0 or 1; $R^2$ is
  (1) when n=1, phenyl or substituted phenyl, and
  (2) when n=0, substituted phenyl, in either instance, substituted phenyl being (a) 3,5-dimethylphenyl or (b) a radical of the formula

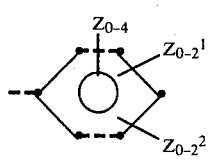

wherein
  each Z independently represents
   (1) Br,
   (2) Cl, or
   (3) F;
  $Z^1$ represents
   (1) $CF_3$,
   (2) $OCF_3$,
   (3) $OC_2F_5$, or
   (4) $OCF_2CF_2H$; and
  $Z^2$ represents
   (1) methyl,
   (2) ethyl, or
   (3) methoxy;
with the further limitation that the entire substituted phenyl radical bears
  (1) at least one Z or $Z^1$,
  (2) not more than 4 substituents, when all substituents are halo substituents;
  (3) not more than 3 substituents, when any one substituent is other than halo; and
  (4) not more than 2 different substituents;
and wherein positions on the pyridine ring are as follows:

(1) the nitrogen to pyridine bond is at the 2-position of the pyridine ring, the $-R^2-(CH_2)_n-R^3$ group is at the 5-position of the pyridine ring, and any $R^1$ is at the 4- or 6-position of the pyridine ring; or (2) the nitrogen to pyridine bond is at the 3-position of the pyridine ring, the $-R^2-(CH_2)_n-R^3$ group is at the 6-position of the pyridine ring, and any $R^1$ is at the 5-position of the pyridine ring;

and the acid addition salts and N-oxides thereof.

The present invention is also directed to

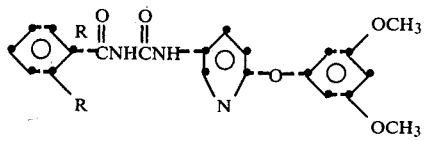

compounds wherein, as above, each R is independently chloro, fluoro, methyl, or methoxy.

Finally, the present invention is directed to methods employing and compositions comprising the above compounds as insecticides.

DETAILED DESCRIPTION OF THE INVENTION

For the purposes of the present application, the compounds of this invention are named as substituted ureas, with numbering as follows:

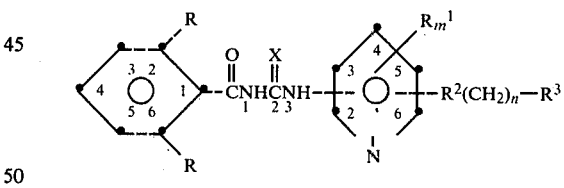

Thus, the comounds are named as 1-(2-substituted or 2,6-disubstituted benzoyl)-3-(substituted pyridinyl)-ureas, N-oxides thereof, or acid addition salts thereof.

The compounds of the present invention are readily prepared by the reaction of a benzoyl isocyanate or benzoyl isothiocyanate of the formula

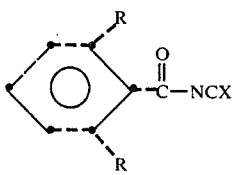

with an aminopyridine of the formula

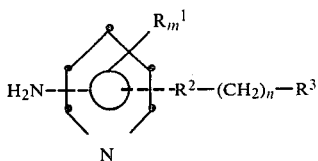

or an N-oxide thereof. The reaction is a known type of reaction, cf. U.S. Pat. No. 3,748,356. The reaction is conveniently conducted in an organic solvent such as ethyl acetate, at room temperature, and with equi-molar amounts of the reactants.

The acid addition salts are prepared by reacting a benzoyl urea or benzoyl thiourea product with the desired acid, in conventional procedures. Acids having a pKa of 3.0 or lower are preferred, and generally the mineral acids are preferred.

The benzoyl isocyanates which serve as starting materials are prepared by the reaction of the corresponding benzamide with oxalyl chloride by the method of Speziale et al., *J. Org. Chem.* 27, 3742 (1962). The benzoyl isothiocyanates are prepared in known procedures by reacting the corresponding benzoyl chlorides with an inorganic thiocyanate, such as ammonium thiocyanate, lead thiocyanate, etc.

The aminopyridines to be employed as starting materials are prepared from the corresponding halonitropyridines:

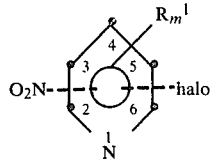

The halonitropyridine is condensed with a phenol, thiophenol, benzyl alcohol, or benzyl mercaptan of the formula $HR^2$—$(CH_2)_n$—$R^3$ and the resulting nitro compound

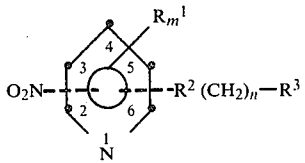

is reduced. The former reaction is conducted in a solvent such as DMF, DMSO, etc. and in the presence of a base, such as triethylamine, KOH, LiOH, etc, to serve as a hydrogen halide acceptor. Preferred conditions are equimolar amounts of the reactants in DMF, at room temperature, and with lithium hydroxide as base. The reduction can be carried out in any of various prior art procedures, including $SnCl_2$/HCl, catalytic hydrogenation, and powered iron with ammonium chloride. Preferred conditions are powdered iron and ammonium chloride.

Many of the halonitropyridines are commercially available and all are prepared by known procedures. The 6-halo-3-nitropyridines, bearing an $R^1$ substituent if desired, are readily prepared by the methods of Acharya et al., *Chem. Abst.* 58, 5623c (1963), Battowski, *Chem. Abst.* 70, 106327x (1969), and Hawkins et al., *J. Org. Chem.* 14, 328 (1949). The 5-halo-2-nitropyridines are also readily prepared, by bromination of a 2-aminopyridine to a 2-amino-5-bromopyridine, in accordance with the procedure of *Org. Syn. Coll.* 5, 346 (John Wiley and Sons, N.Y., 1973); the 2-aminopyridine can also bear an $R^1$ substituent at the 4- or 6-position, in accordance with the definition of the final products of the present invention. Although condensation with a $HR^2$—$(CH_2)_n$—$R^3$ compound bearing electron donating substituents can be carried out directly with a 2-amino-5-bromopyridine (see Example 18, below), the 2-amino-5-bromopyridine compound can also be oxidized to the corresponding 5-bromo-2-nitropyridine compound, which undergoes the condensation regardless of the identity of substituents.

The aminopyridine oxides are prepared in prior art procedures, see Deady, *Synthetic Communications* 7(8), 509–514 (1977) and *Oxidation*, ed. by Augustine, especially Chapter 5 (Marcel Dekker, Inc., N.Y. 1969).

These and numerous other synthesis of pyridine compounds are well known in the literature and are well reviewed in *Pyridine and Its Derivatives*, ed. by Klingsberg, especially Parts 2 and 3 (Interscience Publishers, Inc., N.Y., 1961 and 1962).

Many of the phenols, thiophenols, benzyl alcohols, and benzyl mercaptans which serve as starting materials are also commercially available. All can be prepared in prior art procedures. A convenient procedure for the conversion of a phenol to a thiophenol, or a benzyl alcohol to a benzyl mercaptan, is that of Newman et al., *J. Org. Chem.* 31, 3980 (1966).

Preferred compounds of the present invention are those wherein (1) R in both occurences is the same moiety and is chloro, fluoro, or methoxy; (2) X represents oxygen; (3) $R^2$ represents O or S; (4) the nitrogen to pyridine bond is at the 3-position of the pyridine ring, the —$R^2$—$(CH_2)_n$—$R^3$ group is at the 6-position, and any $R^1$ is at the 5-position; and (5) $R^3$, in the formula —$R^2$—$(CH_2)_n$—$R^3$, is
phenyl (when n=1),
3-bromophenyl,
4-bromophenyl,
3-chlorophenyl,
4-chlorophenyl,
2,4-dichlorophenyl,
2,5-dichlorophenyl,
3,4-dichlorophenyl,
3,5-dichlorophenyl,
3-(trifluoromethyl)phenyl,
4-(trifluoromethyl)phenyl,
3,5-bis(trifluoromethyl)phenyl,
3-(trifluoromethyl)-4-chlorophenyl,
4-(trifluoromethyl)-3-chlorophenyl,
4-fluorophenyl,
2,3,5,6-tetrafluorophenyl,
3-methyl-4-chlorophenyl,
3-methyl-4-bromophenyl, or
2-chloro-5-(trifluoromethyl)phenyl.

The following examples illustrate the synthesis of the compounds of the present invention.

EXAMPLE 1

6-(4-CHLOROPHENYLTHIO)3-NITROPYRIDINE

6-Chloro-3-nitropyridine (4.0 grams) and 4-chlorothiophenol (3.7 grams) were mixed in 100 ml. of dry DMF and lithium hydroxide (1.2 grams) added portionwise. After the reaction mixture had stirred for about 5 minutes, it darkened and became warm. It was allowed to stir with a drying tube for 4 hours, poured over ice water and the product separated by filtration. It was crystallized from ethyl acetate-ethanol, yield: 5.0 grams, m.p. 134°–136° C.

Calc. for $C_{11}H_7ClN_2O_2S$: C, 49.54; H, 2.56; N, 10.50. Found: C, 49.82; H, 2.36; N, 10.60.

EXAMPLE 2
6-(3,5-DIMETHYLPHENOXY)-NITROPYRIDINE

6-Chloro-3-nitropyridine (9.5 grams; 0.06 mole), 3,5-dimethylphenol (7.2 grams; 0.06 mole), and lithium hydroxide (4.0 grams) were mixed in 100 ml. of dimethyl sulfoxide, and the reaction mixture was stirred overnight (about 17 hours) at room temperature. The reaction mixture was then poured into ice water. The product was separated by filtration and crystallized from ethyl acetate-hexanes, yield: 9.5 grams, m.p. 94°–95° C.

Calc. for $C_{13}H_{12}N_2O_3$: C, 63.93; H, 4.93; N, 11.47 Found: C, 63.80; H, 5.03; N, 11.64.

EXAMPLE 3
6-(4-CHLOROPHENYLTHIO)-3-AMINOPYRIDINE 6-(4-Chlorophenylthio)-3-nitropyridine (1.33 grams) was mixed with ammonium chloride (5.0 grams) in 5 ml. of water and about 50 ml. of 3A ethanol at 70°–80° C. Iron powder (3.0 grams) was added portionwise and the reaction mixture heated at 70°–80° C. with constant stirring, for 4 hours. The solution was filtered hot, solvents were removed, and the residue was washed with water; chloroform used to extract the compound was removed in vacuo. A thick oil was crystallized from ether-hexanes after passing through a flush with ethyl acetate on silica gel. The product precipitated as a white solid, yield 1.0 g., m.p. 55°–57°.

Calc. for $C_{11}H_9ClN_2S$: C, 55.81; H, 3.83; N, 11.83. Found: C, 55.64; H, 3.82; N, 12.02.

EXAMPLE 4
6-(4-CHLOROPHENYLTHIO)-3-AMINOPYRIDINE

6-Chloro-3-nitropyridine (54.5 grams), 4-chlorothiophenol (50.0 grams), and lithium hydroxide (12.5 grams) were mixed in about 500 ml. of DMF and stirred overnight (about 18 hours) at room temperature. The reaction mixture was poured into ice-water, filtered, and the separated product washed three times with water and air dried, yield, 100 grams.

The product, without purification, was suspended in a mixture of 1 liter of 3A ethanol and 200 ml. of water. Ammonium chloride (400 grams) and powdered iron (250 grams) were added and the reaction mixture heated to reflux. The reaction became exothermic and refluxed without external heat, for one hour; external heat has supplied and the reaction mixture was refluxed for another hour. The reaction mixture was then filtered hot through Hyflo Super Cel (a diatomaceous earth), extracted with ethyl acetate, washed with water, and solvent removed, yield 58.0 grams. Identity of the product was confirmed by comparison of the NMR with the NMR of an authenic sample.

EXAMPLE 5
6-(4-CHLOROPHENYLSULFONYL)-3-NITROPYRIDINE

Hydrogen peroxide (30%) was added portionwise at room temperature to a solution of 6-(4-chlorophenylthio)-3-nitropyridine (15.7 grams; 0.06 mole) in about 100 ml. of acetic acid. The reaction mixture was then stirred for 10 hours at 70° C. TLC showed 2 spots. Additional hydrogen peroxide was added and the reaction mixture warmed slightly in a water bath. The product precipitated and was separated by filtration and crystallized from ethanol, yield, 12.7 grams, m.p. 177°–180° C.

Calc. for $C_{11}H_7ClN_2O_4S$: C, 44.23; H, 2.36; N, 9.38. Found: C, 44.47; H, 2.29; N, 9.37.

EXAMPLE 6
6-(3-(TRIFLUOROMETHYL)PHENYLSULFINYL)-3-AMINOPYRIDINE 6-(3-(Trifluoromethyl)phenylthio)-3-aminopyridine (4.0 grams) was dissolved in 50 ml. of acetone and m-chloroperoxybenzoic acid (4.0 grams) added. The solution was allowed to stir at room temperature for 2 hours, and an additional 1.0 gram of m-chloroperoxybenzoic acid was added. The reaction mixture was passed over a column of silica gel with ethyl acetate, and the fraction corresponding to the product collected and crystallized from ethyl acetate-hexanes, yield, 4.0 grams m.p. 74°–76° C.

Calc. for $C_{12}H_9F_3N_2OS$: C, 50.35; H, 3.15; N, 9.79. Found: C, 50.08; H, 3.31; N, 9.84.

EXAMPLE 7
2,6-DICHLOROBENZOYL ISOCYANATE

A one-liter flask was purged with nitrogen while dry 2,6-dichlorobenzamide (125 grams, 0.64 mole) and dry toluene (300 ml.) were added. The nitrogen purge was continued as oxalyl chloride (100 grams, 0.79 mole) was added over a 15-minute period, with stirring. The reaction mixture was then heated to 55° C. and stirred overnight (about 18 hours) at 55° C.

The reaction mixture was then heated to reflux (111° C.) and refluxed for 2 hours. Solvent was removed under vacuum and the product distilled off at 134°–135° C. flask temperature and 131°–132° C. vapor temperature, at 13 mm. vacuum, yield 127.5 grams (92.5%).

Calc. for $C_{19}H_{12}Cl_2N_3O_2S$: C, 50.41; H, 2.67; N, 9.28. Found: C, 50.54; H, 2.97; N, 9.45.

EXAMPLE 8
1-(2,6-DICHLOROBENZOYL)-3-(6-(4-CHLOROPHENYLTHIO)-3-PYRIDINYL)UREA 2,6-Dichlorobenzoyl isocyanate (2.16 grams; 0.01 mole) and 6-(4-chlorophenylthio)-3-aminopyridine (2.37 grams; 0.01 mole) were mixed in dry ethyl acetate and stirred for 4 hours. The ethyl acetate was removed in vacuo. TLC showed a 3-spot mixture. The reaction mixture was then poured over a silica column with ethyl acetate, and the major spot collected. It was crystallized from ethyl acetate-hexanes, yield 1.5 g., m.p. 160°–162° C.

Calc. for $C_{19}H_{12}Cl_3N_3O_2S$: C, 50.41; H, 2.67; N, 9.28. Found: C, 50.54; H, 2.97; N, 9.45.

EXAMPLE 9

1-(2,6-DIMETHOXYBENZOYL)-3-(6-(4-CHLOROPHENYLTHIO)-3-PYRIDINYL)UREA 2,6-Dimethoxybenzoyl isocyanate (2.07 grams; 0.01 mole) and 6-(4-chlorophenylthio)-3-aminopyridine (2.37 grams; 0.01 mole) were mixed in 100 ml. of ethyl acetate and stirred at room temperature for 3 hours. Solvent was removed in vacuo and the product crystallized from hexanes-ethyl acetate, yield 0.6 gram, m.p. 172°–174° C.

Calc. for $C_{21}H_{18}ClN_3O_4S$: C, 56.82; H, 4.09; N, 9.47. Found: C, 56.66; H, 3.85; N, 9.64.

EXAMPLE 10

1-(2,6-DIMETHOXYBENZOYL)-3-(6-(4-BROMOPHENOXY)-3-PYRIDINYL)UREA 2,6-Dimethoxybenzoyl isocyanate (2.0 grams) and 6-(4-bromophenoxy)-3-aminopyridine (2.3 grams) were mixed in about 50 ml. of ethyl acetate at room temperature, and the reaction mixture stirred overnight (about 17 hours) at room temperature. The product was separated by filtration and crystallized from a mixture of ethyl acetate and ethanol, yield 0.9 gram, m.p., 177°–179° C.

Calc. for $C_{21}H_{18}BrN_3O_5$: C, 53.41; H, 3.84; N, 8.90. Found: C, 53.19; H, 4.05; N, 9.02.

EXAMPLE 11

1-(2,6-DIMETHYLBENZOYL)-3-(6-(4-CHLOROPHENYLTHIO)-3-PYRIDINYL)UREA 2,6-Dimethylbenzoyl isocyanate (1.61 grams; 0.01 mole) and 6-(4-chlorophenylthio)-3-aminopyridine (2.36 grams; 0.01 mole) were mixed in 50 ml. of ethyl acetate and stirred at room temperature for 12 hours. Solvent was removed in vacuo. TLC showed four spots. The mixture was passed over a column of silica gel with a 1:1 mixture of toluene-ethyl acetate and the product ($R_f \cong 0.7$) separated and crystallized from ethyl acetate-hexanes, yield 1.1 grams, m.p. 159°–160° C.

Calc. for $C_{21}H_{18}ClN_3O_2S$: C, 61.23; H, 4.40; N, 10.20. Found: C, 61.48; H, 4.70; N, 10.34.

EXAMPLE 12

1-(2,6-DICHLOROBENZOYL)-3-(6-(4-CHLOROPHENYLTHIO)-3-PYRIDINYL)UREA, HYDROCHLORIDE SALT 1-(2,6-Dichlorobenzoyl)-3-(6-(4-chlorophenylthio)-3-pyridinyl)urea (2.0 grams) was refluxed in 100 ml. of concentrated HCl (37%) for 4 hours. The reaction mixture was cooled and the product separated by filtration, yield 1.5 grams, m.p., 214°–217° C.

Calc. for $C_{19}H_{13}Cl_4N_3O_2S$: C, 46.65; H, 2.68; N, 8.59. Found: C, 46.90; H, 2.68; N, 8.44.

EXAMPLE 13

1-(2-CHLOROBENZOYL)-3-(6-(3-(TRIFLUOROMETHYLPHENYLTHIO)-3-PYRIDINYL)THIOUREA 6-(3-(Trifluoromethyl)phenylthio)-3-aminopyridine (1.0 gram) and 2-chlorobenzoyl isothiocyanate (1.0 gram) were mixed in 50 ml. of ethyl acetate and stirred overnight (about 18 hours) at room temperature. Solvents were then removed by evaporation and the product residue was crystallized from ethyl acetate-hexanes, m.p. 134°–137° C., yield 1.7 grams.

Calc. for $C_{20}H_{13}ClF_3N_3OS_2$: C, 51.34; H, 2.80; N, 8.98. Found: C, 51.35; H, 2.93; N, 9.06.

EXAMPLE 14

2-NITRO-5-CHLOROPYRIDINE

2-Amino-5-chloropyridine (50 grams) was added portionwise to a solution of 300 ml. of concentrated $H_2SO_4$ and 150 ml. of 30% $H_2O_2$, maintained at a temperature of 0°–5° C., over a period of 5.0 hours. The reaction mixture was then allowed to rise to room temperature and stirred at room temperature for 24 hours. The reaction mixture was then poured over ice, and the product residue separated by filtration and air dried. Crystallization from ethyl acetae-ethanol gave only the azo compound. The remainder of the product residue was passed over a column of silica gel with a mixture of 1:1 toluene:ethyl acetate. The desired product was isolated and its identity confirmed by NMR.

EXAMPLE 15

2-NITRO-5-(4-CHLOROPHENYLTHIO)PYRIDINE

2-Nitro-5-chloropyridine (9.5 grams), 4-chlorothiophenol (8.7 grams), and lithium hydroxide (4 grams) were mixed in 100 ml. of DMF and the reaction mixture was stirred overnight (about 18 hours) at room temperature. The reaction mixture was then poured into water and the product separated by filtration and crystallized from ethanol-hexanes, yield, 10.0 grams, m.p., 96°–98° C.

Calc. for $C_{11}H_7ClN_2O_2S$: C, 49.54; H, 2.65; N, 10.50. Found: C, 49.31; H, 2.88; N, 10.38.

EXAMPLE 16

2-AMINO-5-(4-CHLOROPHENYLTHIO)PYRIDINE

2-Nitro-5-(4-chlorophenylthio)pyridine (10.5 grams), ammonium chloride (50.0 grams), and powdered iron (30.0 grams) were reacted in the same procedures reported in Example 3. The reaction mixture was filtered hot solvents were removed. The product was extracted with ethyl acetate, washed with water, the ethyl acetate removed, and the product crystallized from ethyl acetate-hexanes, yield 4.5 grams, m.p. 157°–159° C.

Calc. for $C_{11}H_9ClN_2S$: C, 55.81; H, 3.83; N, 11.83. Found: C, 55.97; H, 3.88; N, 11.57.

EXAMPLE 17

2-AMINO-5-BROMOPYRIDINE

Bromine (240 grams) was added dropwise to a solution of 2-aminopyridine (141 grams) in 1 liter of acetic acid, maintaining the temperature at 0° C. After the completion of the addition, the temperature of the reaction mixture was raised to 50° C. and the reaction mixture stirred for one hour at that temperature, then poured into water. The precipitate was separated by filtration, and the reaction mixture neutralized with concentrated NaOH and a second precipitate separated by filtration.

NMR established that the first precipitate was 2-amino-3,5-dibromopyridine, whereas the second precipitate was the desired 2-amino-5-bromopyridine, yield, 100 grams, m.p., 130°–132° C. (lit. ref., *Org. Syn. Coll.* 5, supra, m.p., 132°–135° C.).

EXAMPLE 18

2-AMINO-5-(4-CHLOROPHENYLTHIO)PYRIDINE

2-Amino-5-bromopyridine (7.8 grams), 4-chlorothiophenol (9.2 grams), sodium methoxide (3.5 grams), and copper powder (1.0 gram) were reacted in 100 ml. of methanol, for 12 hours, in a bomb, in accordance with the procedures of *J. Med. Chem.* 21, 235 (1978). The reaction mixture was filtered, washed with methanol, and methanol removed by evaporation. The methanol washes were combined with ethyl acetate extracts of solids made after refluxing on a steam bath for one hour. Solvents were removed and the solids dissolved in ethyl acetate and filtered to remove insolubles. The liquid was passed over a silica column with ethyl acetate, and the fraction corresponding to the product amine ($R_f \cong 0.2$) collected., yield 6.5 grams, m.p., 161°–163° C.

Calc. for $C_{11}H_9ClN_2S$: C, 55.81; H, 3.83; N, 11.83. Found: C, 55.87; H, 4.02; N, 11.83.

Other representative compounds of the present invention include the following.

| Example No. | Compound Name | Melting Point (C.) |
|---|---|---|
| 19 | 1-(2,6-Dichlorobenzoyl)-3-(6-(4-bromophenylthio)-3-pyridinyl)urea | 184–186° |
| 20 | 1-(2,6-Dimethoxybenzoyl)-3-(6-(4-bromophenylthio)-3-pyridinyl)urea | 174–176° |
| 21 | 1-(2,6-Dichlorobenzoyl)-3-(6-(3,4-dichlorophenylthio)-3-pyridinyl)urea | 168–171° |
| 22 | 1-(2,6-Dichlorobenzoyl)-3-(6-(4-bromo-3-methylphenylthio)-3-pyridinyl)urea | 175–177° |
| 23 | 1-(2,6-Dimethoxybenzoyl)-3-(6-(3,4-dichlorophenylthio)-3-pyridinyl)urea | 145–149° |
| 24 | 1-(2,6-Dimethoxybenzoyl)-3-(6-(4-chlorophenoxy)-3-pyridinyl)urea | 184–187° |
| 25 | 1-(2,6-Dimethoxybenzoyl)-3-(6-(4-bromo-3-methylphenylthio)-3-pyridinyl)urea | 180–182° |
| 26 | 1-(2,6-Dichlorobenzoyl)-3-(6-(4-chlorophenoxy)-3-pyridinyl)urea | 203–205° |
| 27 | 1-(2,6-Dichlorobenzoyl)-3-(6-(3,4-dichlorophenoxy)-3-pyridinyl)urea | 200–202° |
| 28 | 1-(2,6-Dichlorobenzoyl)-3-(6-(3-(trifluoromethyl)phenylthio)-3-pyridinyl)urea | 179–181° |
| 29 | 1-(2-Chlorobenzoyl)-3-(6-(3-trifluoromethyl)phenylthio)-3-pyridinyl)urea | 145–147° |
| 30 | 1-(2,6-Dichlorobenzoyl)-3-(6-(3-chlorophenoxy)-3-pyridinyl)urea | 189–192° |
| 31 | 1-(2,6-Dimethylbenzoyl)-3-(6-(3,4-dichlorophenoxy)-3-pyridinyl)urea | 160–162° |
| 32 | 1-(2,6-Dimethoxybenzoyl)-3-(6-(3-chlorophenoxy)-3-pyridinyl)urea | 165–168° |
| 33 | 1-(2,6-Dimethoxybenzoyl)-3-(6-(2-chlorophenoxy)-3-pyridinyl)urea | 151–153° |
| 34 | 1-(2,6-Dimethoxybenzoyl)-3-(6-(3-trifluoromethyl)phenylthio)-3-pyridinyl)urea | 118–121° |
| 35 | 1-(2,6-Dimethoxybenzoyl)-3-(6-(3,4-dichlorophenoxy)-3-pyridinyl)urea | 164–166° |
| 36 | 1-(2,6-Dichlorobenzoyl)-3-(6-(4-chloro-3-methylphenoxy)-3-pyridinyl)urea | 172–175° |
| 37 | 1-(2,6-Dimethoxybenzoyl)-3-(6-(2-chlorophenylthio)-3-pyridinyl)urea | 144–146° |
| 38 | 1-(2,6-Dimethoxybenzoyl)-3-(6-(4-chloro-3-methylphenoxy)-3-pyridinyl)urea | 183–185° |
| 39 | 1-(2,6-Dichlorobenzoyl)-3-(6-(4-bromophenoxy)-3-pyridinyl)urea | 200–202° |
| 40 | 1-(2,6-Dichlorobenzoyl)-3-(6-(2-chloro-5-(trifluoromethyl)phenoxy)-3-pyridinyl)urea | 196–198° |
| 41 | 1-(2,6-Dimethoxybenzoyl)-3-(6-(2-chloro-5-(trifluoromethyl)phenoxy)-3-pyridinyl)urea | 198–202° |
| 42 | 1-(2,6-Dimethoxybenzoyl)-3-(6-(4-chlorobenzylthio)-3-pyridinyl)urea | 192–195° |
| 43 | 1-(2,6-Dichlorobenzoyl)-3-(6-(4-chlorobenzylthio)-3-pyridinyl)urea | 140–143° |
| 44 | 1-(2,6-Dimethoxybenzoyl)-3-(6-(3,4-dichlorobenzylthio)-3-pyridinyl)urea | 117–120° |
| 45 | 1-(2,6-Dichlorobenzoyl)-3-(6-(3-(trifluoromethyl)benzyloxy)-3-pyridinyl)urea | 165–167° |
| 46 | 1-(2,6-Dimethoxybenzoyl)-3-(6-(3-(trifluoromethyl)benzyloxy)-3-pyridinyl)urea | 127–130° |
| 47 | 1-(2,6-Dichlorobenzoyl)-3-(6-(3,4-dichlorobenzylthio)-3-pyridinyl)urea | 173–175° |
| 48 | 1-(2,6-Dimethoxybenzoyl)-3-(6-(4-chlorobenzylsulfonyl)-3-pyridinyl)urea | 194–196° |
| 49 | 1-(2,6-Dichlorobenzoyl)-3-(5-chloro-6-(4-chlorophenylthio)-3-pyridinyl)urea | 196–199° |
| 50 | 1-(2,6-Dimethoxybenzoyl)-3-(5-chloro-6-(4-chlorophenylthio)-3-pyridinyl)urea | 172–174° |
| 51 | 1-(2,6-Dichlorobenzoyl)-3-(6-(3,5-dimethylphenoxy)-3-pyridinyl)urea | 147–149° |
| 52 | 1-(2,6-Dichlorobenzoyl)-3-(6-(3,5-dichlorophenoxy)-5-methyl-3-pyridinyl)urea | 198–201° |
| 53 | 1-(2,6-Dimethoxybenzoyl)-3-(6-(3,5-dimethylphenoxy)-3-pyridinyl)urea | 201–203° |
| 54 | 1-(2,6-Dimethoxybenzoyl)-3-(6-(3,5-dichlorophenoxy)-5-methyl-3-pyridinyl)urea | 216–219° |

-continued

| Example No. | Compound Name | Melting Point (C.) |
|---|---|---|
| 55 | 1-(2,6-Dichlorobenzoyl)-3-(6-(3-(trifluoromethyl)benzylthio)-3-pyridinyl)urea | 125–127° |
| 56 | 1-(2,6-Dimethoxybenzoyl)-3-(6-(3-(trifluoromethyl)benzylthio)-3-pyridinyl)urea | 138–140° |
| 57 | 1-(2,6-Dichlorobenzoyl)-3-(6-(3,4-dichlorobenzyloxy)-3-pyridinyl)urea | 191–193° |
| 58 | 1-(2,6-Dimethoxybenzoyl)-3-(6-(3,4-dichlorobenzyloxy)-3-pyridinyl)urea | 184–186° |
| 59 | 1-(2,6-Dichlorobenzoyl)-3-(6-(3-(trifluoromethyl)phenylsulfinyl)-3-pyridinyl)urea | 210–214° |
| 60 | 1-(2,6-Dimethoxybenzoyl)-3-(6-(3-(trifluoromethyl)phenylsulfinyl)-3-pyridinyl)urea | 109–111° |
| 61 | 1-(2-Chloro-6-methoxybenzoyl)-3-(6-(4-chlorophenylthio)-3-pyridinyl)urea | 147–150° |
| 62 | 1-(2-Chloro-6-methoxybenzoyl)-3-(6-(3-(trifluoromethyl)phenoxy)-3-pyridinyl)urea | 134–138° |
| 63 | 1-(2-Chloro-6-methoxybenzoyl)-3-(6-(3,5-dichlorophenoxy)-3-pyridinyl)urea | 156–159° |
| 64 | 1-(2,6-Dimethoxybenzoyl)-3-(6-(3,4-dichlorophenylsulfonyl)-3-pyridinyl)urea | 187–190° |
| 65 | 1-(2,6-Dichlorobenzoyl)-3-(6-(4-chlorophenylsulfonyl)-3-pyridinyl)urea | 207–210° |
| 66 | 1-(2,6-Dimethoxybenzoyl)-3-(6-(3-chlorophenylthio)-3-pyridinyl)urea | 192–196° |
| 67 | 1-(2,6-Dimethoxybenzoyl)-3-(6-(4-fluorophenylthio)-3-pyridinyl)urea | 167–173° |
| 68 | 1-(2,6-Dichlorobenzoyl)-3-(6-(3-chlorophenylthio)-3-pyridinyl)urea | 168–171° |
| 69 | 1-(2,6-Dimethoxybenzoyl)-3-(6-(4-chlorophenylthio)-5-methyl-3-pyridinyl)urea | 160–163° |
| 70 | 1-(2,6-Dichlorobenzoyl)-3-(6-(4-fluorophenylthio)-3-pyridinyl)urea | 194–196° |
| 71 | 1-(2,6-Dichlorobenzoyl)-3-(6-(4-chlorophenylthio)-5-methyl-3-pyridinyl)urea | 150–154° |
| 72 | 1-(2,6-Dimethoxybenzoyl)-3-(6-benzylthio-3-pyridinyl)urea | 192–194° |
| 73 | 1-(2,6-Dichlorobenzoyl)-3-(6-(3-bromophenoxy)-3-pyridinyl)urea | 192–195° |
| 74 | 1-(2,6-Dichlorobenzoyl)-3-(6-(3-(trifluoromethyl)phenoxy)-3-pyridinyl)urea | 173–175° |
| 75 | 1-(2-Chlorobenzoyl)-3-(6-(3-(trifluoromethyl)phenoxy)-3-pyridinyl)urea | 161–163° |
| 76 | 1-(2,6-Dimethoxybenzoyl)-3-(6-(3-(trifluoromethyl)phenoxy)-3-pyridinyl)urea | 151–153° |
| 77 | 1-(2,6-Dichlorobenzoyl)-3-(6-(2,5-dichlorophenylthio)-3-pyridinyl)urea | 205–208° |
| 78 | 1-(2,6-Dichlorobenzoyl)-3-(6-(4-chlorophenoxy)-5-methyl-3-pyridinyl)urea | 217–219° |
| 79 | 1-(2,6-Dimethoxybenzoyl)-3-(6-(4-chlorophenoxy)-5-methyl-3-pyridinyl)urea | 202–205° |
| 80 | 1-(2,6-Dichlorobenzoyl)-3-(6-(4-chlorophenylsulfonyl)-5-methyl-3-pyridinyl)urea | 189–192° |
| 81 | 1-(2,6-Dimethoxybenzoyl)-3-(6-(4-chlorophenylsulfonyl)-5-methyl-3-pyridinyl)urea | 190–193° |
| 82 | 1-(2,6-Dimethoxybenzoyl)-3-(6-(3,5-dichlorophenoxy)-3-pyridinyl)urea | 173–176° |
| 83 | 1-(2,6-Dichlorobenzoyl)-3-(6-(3-bromophenylthio)-3-pyridinyl)urea | 170–173° |
| 84 | 1-(2,6-Dichlorobenzoyl)-3-(6-(3,5-dichlorophenoxy)-3-pyridinyl)urea | 205–207° |
| 85 | 1-(2,6-Dimethoxybenzoyl)-3-(5-methyl-6-(3-(trifluoromethyl)phenylthio)-3-pyridinyl)urea | 125–127° |
| 86 | 1-(2,6-Dichlorobenzoyl)-3-(6-(4-(trifluoromethyl)phenoxy)-3-pyridinyl)urea | 190–193° |
| 87 | 1-(2,6-Dichlorobenzoyl)-3-(5-methyl-6-(3-(trifluoromethyl)phenylthio)-3-pyridinyl)urea | 184–186° |
| 88 | 1-(2,6-Dimethoxybenzoyl)-3-(6-(2,4-dichlorophenoxy)-3-pyridinyl)urea | 199–202° |
| 89 | 1-(2,6-Dimethoxybenzoyl)-3-(6-(4-(trifluoromethyl)phenoxy)-3-pyridinyl)urea | 163–165° |
| 90 | 1-(2,6-Dichlorobenzoyl)-3-(6-(2,4-dichlorophenylthio)-3-pyridinyl)urea | 202–205° |
| 91 | 1-(2,6-Dimethoxybenzoyl)-3-(6-(2,4-dichlorophenylthio)-3-pyridinyl)urea | 125–129° |
| 92 | 1-(2,6-Dichlorobenzoyl)-3-(6-(3-fluorophenoxy)-3-pyridinyl)urea | 155–158° |
| 93 | 1-(2,6-Dichlorobenzoyl)-3-(6-(4-fluorophenoxy)-3-pyridinyl)urea | 215–217° |
| 94 | 1-(2,6-Dimethoxybenzoyl)-3-(6-(4-fluorophenoxy)-3-pyridinyl)urea | 172–175° |
| 95 | 1-(2,6-Dichlorobenzoyl)-3-(6-(2,4-dichlorophenoxy)-3-pyridinyl)urea | 191–194° |

-continued

| Example No. | Compound Name | Melting Point (C.) |
|---|---|---|
| 96 | 1-(2,6-Dimethoxybenzoyl)-3-(6-(2-fluorophenoxy)-3-pyridinyl)urea | 180–183° |
| 97 | 1-(2,6-Dimethoxybenzoyl)-3-(6-(4-chlorobenzyloxy)-3-pyridinyl)urea | 163–166° |
| 98 | 1-(2,6-Dichlorobenzoyl)-3-(6-(4-chlorobenzyloxy)-3-pyridinyl)urea | 180–183° |
| 99 | 1-(2,6-Dichlorobenzoyl)-3-(6-(2,4-dichlorobenzylthio)-3-pyridinyl)urea | 197–200° |
| 100 | 1-(2,6-Dimethoxybenzoyl)-3-(6-(2,4-dichlorobenzylthio)-3-pyridinyl)urea | 151–154° |
| 101 | 1-(2-Chlorobenzoyl)-3-(6-(2-chloro-5-(trifluoromethyl)phenoxy)-3-pyridinyl)urea | 175–177° |
| 102 | 1-(2,6-Dichlorobenzoyl)-3-(6-benzyloxy-3-pyridinyl)urea | 197–199° |
| 103 | 1-(2,6-Dimethoxybenzoyl)-3-(6-benzyloxy-3-pyridinyl)urea | 172–174° |
| 104 | 1-(2-Chloro-6-methylbenzoyl)-3-(6-(2-chlorophenylthio)-3-pyridinyl)urea | 165–168° |
| 105 | 1-(2,6-Dichlorobenzoyl)-3-(6-(4-chloro-3,5-dimethylphenoxy)-3-pyridinyl)urea | 220–222° |
| 106 | 1-(2,6-Dimethoxybenzoyl)-3-(6-(4-chloro-3,5-dimethylphenoxy)-3-pyridinyl)urea | 188–190° |
| 107 | 1-(2,6-Dimethoxybenzoyl)-3-(6-(2-bromophenoxy)-3-pyridinyl)urea | 180–183° |
| 108 | 1-(2,6-Dimethoxybenzoyl)-3-(6-(3-bromophenoxy)-3-pyridinyl)urea | 185–187° |
| 109 | 1-(2,6-Dichlorobenzoyl)-3-(6-(2-bromophenoxy)-3-pyridinyl)urea | 199–202° |
| 110 | 1-(2,6-Dichlorobenzoyl)-3-(6-(2-bromophenylthio)-3-pyridinyl)urea | 218–221° |
| 111 | 1-(2,6-Dimethoxybenzoyl)-3-(6-(2-bromophenylthio)-3-pyridinyl)urea | 139–141° |
| 112 | 1-(2,6-Dichlorobenzoyl)-3-(6-(2,4,5-trichlorophenylthio)-3-pyridinyl)urea | 212–215° |
| 113 | 1-(2,6-Dimethoxybenzoyl)-3-(6-(2,4,5-trichlorophenylthio)-3-pyridinyl)urea | 190–193° |
| 114 | 1-(2,6-Dichlorobenzoyl)-3-(6-(2-(trifluoromethyl)phenoxy)-3-pyridinyl)urea | 168–171° |
| 115 | 1-(2,6-Dimethoxybenzoyl)-3-(6-(3-bromophenylthio)-3-pyridinyl)urea | 193–196° |
| 116 | 1-(2,6-Dichlorobenzoyl)-3-(6-(2-chlorophenylthio)-3-pyridinyl)urea | 202–205° |
| 117 | 1-(2,6-Dichlorobenzoyl)-3-(6-(3,4,5-trichlorophenoxy)-3-pyridinyl)urea | 230–233° |
| 118 | 1-(2,6-Dichlorobenzoyl)-3-(6-(2-chlorophenoxy)-3-pyridinyl)urea | 187–189° |
| 119 | 1-(2,6-Dimethoxybenzoyl)-3-(6-(2,5-dichlorophenylthio)-3-pyridinyl)urea | 186–189° |
| 120 | 1-(2,6-Dichlorobenzoyl)-3-(6-(2,3,5,6-tetrafluorophenylthio)-3-pyridinyl)urea | 208–211° |
| 121 | 1-(2,6-Dimethoxybenzoyl)-3-(6-(2,3,5,6-tetrafluorophenylthio)-3-pyridinyl)urea | 202–204° |
| 122 | 1-(2,6-Dichlorobenzoyl)-3-(6-(2-fluorophenoxy)-3-pyridinyl)urea | 165–167° |
| 123 | 1-(2-Chlorobenzoyl)-3-(6-(3-(trifluoromethyl)phenylsulfinyl)-3-pyridinyl)urea | 140–145° |
| 124 | 1-(2-Chlorobenzoyl)-3-(6-(3-(trifluoromethyl)phenoxy)-3-pyridinyl)thiourea | 114–115° |
| 125 | 1-(2-Chlorobenzoyl)-3-(5-methyl-6-(3-(trifluoromethyl)phenylthio)-3-pyridinyl)urea | 137–139° |
| 126 | 1-(2,6-Dichlorobenzoyl)-3-(6-(3-chloro-5-methoxyphenoxy)-3-pyridinyl)urea | 140–142° |
| 127 | 1-(2,6-Dimethoxybenzoyl)-3-(6-(3-chloro-5-methoxyphenoxy)-3-pyridinyl)urea | 165–167° |
| 128 | 1-(2,6-Dichlorobenzoyl)-3-(6-(3-(trifluoromethyl)phenylsulfonyl)-3-pyridinyl)urea | 215–218° |
| 129 | 1-(2,6-Difluorobenzoyl)-3-(6-(3-(trifluoromethyl)phenoxy)-3-pyridinyl)urea | 157–159° |
| 130 | 1-(2,6-Difluorobenzoyl)-3-(6-(4-chlorophenylthio)-3-pyridinyl)urea | 205–208° |
| 131 | 1-(2,6-Difluorobenzoyl)-3-(5-methyl-6-(3-(trifluoromethyl)phenylthio)-3-pyridinyl)urea | 134–136° |
| 132 | 1-(2,6-Dichlorobenzoyl)-3-(6-(4-chlorophenylsulfinyl)-3-pyridinyl)urea | 127–129° |
| 133 | 1-(2,6-Dimethoxybenzoyl)-3-(6-(4-chlorophenylsulfinyl)-3-pyridinyl)urea | 183–185° |
| 134 | 1-(2,6-Dichlorobenzoyl)-3-(6-(4-chlorobenzylsulfonyl)-3-pyridinyl)urea | 235–239° |
| 135 | 1-(2-Chlorobenzoyl)-3-(6-(3,5-bis(trifluoromethyl)phenyl)thio)-3-pyridinyl)thiourea | |
| 136 | 1-(2,6-Dichlorobenzoyl)-3-(5-chloro-6-(3-(trifluoromethyl)phenoxy)-3-pyridinyl)urea | 148–151° |
| 137 | 1-(2,6-Dichlorobenzoyl)-3-(6-benzylthio-3-pyridinyl)urea | 140–142° |
| 138 | 1-(2,6-Dimethoxybenzoyl)-3-(5-chloro-6-(3-(trifluoromethyl)phenoxy)-3-pyridinyl)urea | 181–184° |
| 139 | 1-(2,6-Dichlorobenzoyl)-3-(5-(4-chlorophenylthio)-2-pyridinyl)urea | 132–135° |
| 140 | 1-(2,6-Dimethoxybenzoyl)-3-(5-(4-chlorophenylthio)-2-pyridinyl)- | |

-continued

| Example No. | Compound Name | Melting Point (C.) |
|---|---|---|
| | urea | 85–87° |
| 141 | 1-(2,6-Dichlorobenzoyl)-3-(5-(4-chlorophenoxy)-2-pyridinyl)urea | |
| 142 | 1-(2,6-Dimethoxybenzoyl)-3-(5-(4-chlorophenoxy)-2-pyridinyl)urea | |
| 143 | 1-(2,6-Dichlorobenzoyl)-3-(5-(3-(trifluoromethyl)phenylthio)-2-pyridinyl)urea | 170–174° |
| 144 | 1-(2,6-Dimethoxybenzoyl)-3-(5-(3-(trifluoromethyl)phenylthio-2-pyridinyl)urea | 121–124° |
| 145 | 1-(2,6-Dichlorobenzoyl)-3-(5-(3-(trifluoromethyl)phenoxy-2-pyridinyl)urea | |
| 146 | 1-(2,6-Dimethoxybenzoyl)-3-(5-(3-(trifluoromethyl)phenoxy-2-pyridinyl)urea | |
| 147 | 1-(2,6-Dichlorobenzoyl)-3-(5-(3,5-dichlorophenylthio)-2-pyridinyl)urea | |
| 148 | 1-(2,6-Dimethoxybenzoyl)-3-(5-(3,5-dichlorophenylthio)-2-pyridinyl)urea | |
| 149 | 1-(2,6-Dichlorobenzoyl)-3-(5-(3,5-dichlorophenoxy)-2-pyridinyl)urea | |
| 150 | 1-(2,6-Dimethoxybenzoyl)-3-(5-(3,5-dichlorophenoxy)-2-pyridinyl)urea | |
| 151 | 1-(2,6-Dichlorobenzoyl)-3-(5-(2-chloro-5-(trifluoromethyl)phenylthio)-2-pyridinyl)urea | |
| 152 | 1-(2,6-Dimethoxybenzoyl)-3-(5-(2-chloro-5-(trifluoromethyl)phenylthio)-2-pyridinyl)urea | |
| 153 | 1-(2,6-Dichlorobenzoyl)-3-(5-(2-chloro-5-(trifluoromethyl)-phenoxy)-2-pyridinyl)urea | |
| 154 | 1-(2,6-Dimethoxybenzoyl)-3-(5-(2-chloro-5-(trifluoromethyl)-phenoxy)-2-pyridinyl)urea | |
| 155 | 1-(2,6-Dichlorobenzoyl)-3-(5-(3,4-dichlorophenylthio)-2-pyridinyl)urea | 160–163° |
| 156 | 1-(2,6-Dimethoxybenzoyl)-3-(5-(3,4-dichlorophenylthio)-2-pyridinyl)urea | 183–185° |
| 157 | 1-(2,6-Dichlorobenzoyl)-3-(5-(3,4-dichlorophenoxy)-2-pyridinyl)urea | |
| 158 | 1-(2,6-Dimethoxybenzoyl)-3-(5-(3,4-dichlorophenoxy)-2-pyridinyl)urea | |
| 159 | 1-(2,6-Dichlorobenzoyl)-3-(5-(3,5-bis(trifluoromethyl)phenylthio)-2-pyridinyl)urea | |
| 160 | 1-(2,6-Dimethoxybenzoyl)-3-(5-(3,5-bis(trifluoromethyl)phenylthio)-2-pyridinyl)urea | |
| 161 | 1-(2,6-Dichlorobenzoyl)-3-(5-(3,5-bis(trifluoromethyl)phenoxy)-2-pyridinyl)urea | |
| 162 | 1-(2,6-Dimethoxybenzoyl)-3-(5-(3,5-bis(trifluoromethyl)phenoxy)-2-pyridinyl)urea | |
| 163 | 1-(2,6-Dichlorobenzoyl)-3-(5-(3-chloro-4-(trifluoromethyl)-phenylthio)-2-pyridinyl)urea | |
| 164 | 1-(2,6-Dimethoxybenzoyl)-3-(5-(3-chloro-4-(trifluoromethyl)-phenylthio)-2-pyridinyl)urea | |
| 165 | 1-(2,6-Dichlorobenzoyl)-3-(5-(3-chloro-4-(trifluoromethyl)-phenoxy)-2-pyridinyl)urea | |
| 166 | 1-(2,6-Dimethoxybenzoyl)-3-(5-(3-chloro-4-(trifluoromethyl)-phenoxy)-2-pyridinyl)urea | |
| 167 | 1-(2,6-Dichlorobenzoyl)-3-(5-(4-chloro-3-(trifluoromethyl)-phenylthio)-2-pyridinyl)urea | |
| 168 | 1-(2,6-Dimethoxybenzoyl)-3-(5-(4-chloro-3-(trifluoromethyl)-phenylthio)-2-pyridinyl)urea | |
| 169 | 1-(2,6-Dichlorobenzoyl)-3-(5-(4-chloro-3-(trifluoromethyl)-phenoxy)-2-pyridinyl)urea | |
| 170 | 1-(2,6-Dimethoxybenzoyl)-3-(5-(4-chloro-3-(trifluoromethyl)-phenoxy)-2-pyridinyl)urea | |
| 171 | 1-(2,6-Dichlorobenzoyl)-3-(5-benzylthio-2-pyridinyl)urea | |
| 172 | 1-(2,6-Dimethoxybenzoyl)-3-(5-benzylthio-2-pyridinyl)urea | |
| 173 | 1-(2,6-Dichlorobenzoyl)-3-(5-benzyloxy-2-pyridinyl)urea | |
| 174 | 1-(2,6-Dimethoxybenzoyl)-3-(5-benzyloxy-2-pyridinyl)urea | |
| 175 | 1-(2,6-Dichlorobenzoyl)-3-(5-(2,4-dichlorobenzylthio)-2-pyridinyl)urea | |
| 176 | 1-(2,6-Dimethoxybenzoyl)-3-(5-(2,4-dichlorobenzylthio)-2-pyridinyl)urea | |
| 177 | 1-(2,6-Dichlorobenzoyl)-3-(5-(2,4-dichlorobenzyloxy)-2-pyridinyl)urea | |
| 178 | 1-(2,6-Dimethoxybenzoyl)-3-(5-(2,4-dichlorobenzyloxy)-2-pyridinyl)urea | |
| 179 | 1-(2,6-Dichlorobenzoyl)-3-(6-(3-chloro-4-(trifluoromethyl)-phenylthio)-3-pyridinyl)urea | |
| 180 | 1-(2,6-Dimethoxybenzoyl)-3-(6-(3-chloro-4-(trifluoromethyl)-phenylthio)-3-pyridinyl)urea | |
| 181 | 1-(2,6-Dichlorobenzoyl)-3-(6-(3-chloro-4-(trifluoromethyl)-phenoxy)-3-pyridinyl)urea | |
| 182 | 1-(2,6-Dimethoxybenzoyl)-3-(6-(3-chloro-4-(trifluoromethyl)-phenoxy)-3-pyridinyl)urea | |
| 183 | 1-(2,6-Dichlorobenzoyl)-3-(6-(4-chloro-3-(trifluoromethyl)- | |

-continued

| Example No. | Compound Name | Melting Point (C.) |
|---|---|---|
| 184 | 1-(2,6-Dimethoxybenzoyl)-3-(6-(4-chloro-3-(trifluoromethyl)-phenylthio)-3-pyridinyl)urea | |
| 185 | 1-(2,6-Dichlorobenzoyl)-3-(6-(4-chloro-3-(trifluoromethyl)-phenoxy)-3-pyridinyl)urea | 221–224° |
| 186 | 1-(2,6-Dimethoxybenzoyl)-3-(6-(4-chloro-3-(trifluoromethyl)-phenoxy)-3-pyridinyl)urea | 125–127° |
| 187 | 1-(2,6-Dichlorobenzoyl)-3-(6-(3,5-bis(trifluoromethyl)phenyl-thio)-3-pyridinyl)urea | |
| 188 | 1-(2,6-Dimethoxybenzoyl)-3-(6-(3,5-bis(trifluoromethyl)phenyl-thio)-3-pyridinyl)urea | |
| 189 | 1-(2,6-Dichlorobenzoyl)-3-(6-(3,5-bis(trifluoromethyl)phenoxy)-3-pyridinyl)urea | |
| 190 | 1-(2,6-Dimethoxybenzoyl)-3-(6-(3,5-bis(trifluoromethyl)phenoxy)-3-pyridinyl)urea | |
| 191 | 1-(2,6-Dichlorobenzoyl)-3-(6-(3-chloro-5-(trifluoromethyl)phenyl-thio-3-pyridinyl)urea | |
| 192 | 1-(2,6-Dimethoxybenzoyl)-3-(6-(3-chloro-5-(trifluoromethyl)-phenylthio)-3-pyridinyl)urea | |
| 193 | 1-(2,6-Dichlorobenzoyl)-3-(6-(3-chloro-5-(trifluoromethyl)-phenoxy)-3-pyridinyl)urea | |
| 194 | 1-(2,6-Dimethoxybenzoyl)-3-(6-(3-chloro-5-(trifluoromethyl)-phenoxy)-3-pyridinyl)urea | |
| 195 | 1-(2,6-Dichlorobenzoyl)-3-(5-(3-chloro-5-(trifluoromethyl)-phenylthio)-2-pyridinyl)urea | |
| 196 | 1-(2,6-Dimethoxybenzoyl)-3-(5-(3-chloro-5-(trifluoromethyl)-phenylthio)-2-pyridinyl)urea | |
| 197 | 1-(2,6-Dichlorobenzoyl)-3-(5-(3-chloro-5-(trifluoromethyl)-phenoxy)-2-pyridinyl)urea | |
| 198 | 1-(2,6-Dimethoxybenzoyl)-3-(5-(3-chloro-5-(trifluoromethyl)-phenoxy)-2-pyridinyl)urea | |
| 199 | 1-(2,6-Dichlorobenzoyl)-3-(6-(3,5-dichlorophenylthio)-3-pyridinyl)urea | 170–173° |
| 200 | 1-(2,6-Dimethoxybenzoyl)-3-(6-(3,5-dichlorophenylthio)-3-pyridinyl)urea | 203–206° |
| 201 | 1-(2,6-Dimethoxybenzoyl)-3-(6-(2,3-dichlorophenoxy)-3-pyridinyl)urea | 173–174° |
| 202 | 1-(2,6-Dichlorobenzoyl)-3-(6-(2,4-dibromophenoxy)-3-pyridinyl)urea | 219–221° |
| 203 | 1-(2,6-Dimethoxybenzoyl)-3-(6-(2,4-dibromophenoxy)-3-pyridinyl)urea | 186–189° |
| 204 | 1-(2,6-Dichlorobenzoyl)-3-(6-(2,4-dichlorobenzyloxy)-3-pyridinyl)urea | 195–197° |
| 205 | 1-(2,6-Dimethoxybenzoyl)-3-(6-(2,4-dichlorobenzyloxy)-3-pyridinyl)urea | 177–181° |
| 206 | 1-(2,6-Dichlorobenzoyl)-3-(6-(2,6-dichlorophenoxy)-3-pyridinyl)urea | 235–237° |
| 207 | 1-(2,6-Dimethoxybenzoyl)-3-(6-(2,6-dichlorophenoxy)-3-pyridinyl)urea | 241–244° |
| 208 | 1-(2,6-Dichlorobenzoyl)-3-(6-(3,5-dichlorobenzyloxy)-3-pyridinyl)urea | 209–211° |
| 209 | 1-(2,6-Dimethoxybenzoyl)-3-(6-(3,5-dichlorobenzyloxy)-3-pyridinyl)urea | 223–226° |
| 210 | 1-(2,6-Dichlorobenzoyl)-3-(6-(3,5-dichlorophenylsulfonyl)-3-pyridinyl)urea | 228–230° |
| 211 | 1-(2,6-Dichlorobenzoyl)-3-(6-(4-bromo-2,5-dichlorophenoxy)-3-pyridinyl)urea | 243–245° |
| 212 | 1-(2,6-Dimethoxybenzoyl)-3-(6-(4-bromo-2,5-dichlorophenoxy)-3-pyridinyl)urea | 205–208° |
| 213 | 1-(2,6-Dichlorobenzoyl)-3-(6-(2-chloro-5-(trifluoromethyl)-phenylthio)-3-pyridinyl)urea | 146–150° |
| 214 | 1-(2,6-Dimethoxybenzoyl)-3-(6-(2-chloro-5-(trifluoromethyl)-phenylthio)-3-pyridinyl)urea | 187–190° |
| 215 | 1-(2,6-Dichlorobenzoyl)-3-(6-(2-chloro-5-(trifluoromethyl)-phenylsulfonyl)-3-pyridinyl)urea | 243–246° |
| 216 | 1-(2,6-Dichlorobenzoyl)-3-(6-(2-chloro-5-methylphenoxy)-3-pyridinyl)urea | 166–168° |
| 217 | 1-(2,6-Dimethoxybenzoyl)-3-(6-(2-chloro-5-methylphenoxy)-3-pyridinyl)urea | 177–181° |
| 218 | 1-(2-Chloro-6-methoxybenzoyl)-3-(6-2,4-dichlorobenzyloxy)-3-pyridinyl)urea | 185–188° |
| 219 | 1-(2-Chloro-6-methoxybenzoyl)-3-(6-(2-chloro-5-(trifluoro-methyl)phenoxy)-3-pyridinyl)urea | 158–161° |
| 220 | 1-(2,6-Difluorobenzoyl)-3-(6-(2,4-dichlorobenzyloxy)-3-pyridinyl)urea | 199–202° |
| 221 | 1-(2,6-Difluorobenzoyl)-3-(6-(2-chloro-5-(trifluoromethyl)-phenoxy)-3-pyridinyl)urea | 180–184° |
| 222 | 1-(2,6-Difluorobenzoyl)-3-(6-(3,5-dichlorophenoxy)-3-pyridinyl)urea | 190–194° |
| 223 | 1-(2-Chloro-6-methoxybenzoyl)-3-(6-(3-chloro-5-methoxyphenoxy)- | |

-continued

| Example No. | Compound Name | Melting Point (C.) |
|---|---|---|
| | 3-pyridinyl)urea | 40–43° |
| 224 | 1-(2-Chloro-6-methoxybenzoyl)-3-(6-(4-chlorophenylsulfonyl)-3-pyridinyl)urea | 60–62° |
| 225 | 1-(2-Chloro-6-fluorobenzoyl)-3-(6-(2-chloro-5-(trifluoromethyl)phenoxy)-3-pyridinyl)urea | 157–160° |
| 226 | 1-(2-Chloro-6-fluorobenzoyl)-3-(6-(2,4-dichlorobenzyloxy)-3-pyridinyl)urea | 187–190° |
| 227 | 1-(2-Chloro-6-fluorobenzoyl)-3-(6-(3-(trifluoromethyl)phenoxy)-3-pyridinyl)urea | 104–107° |
| 228 | 1-(2-Chloro-6-fluorobenzoyl)-3-(6-(3,5-dichlorophenoxy)-3-pyridinyl)urea | 183–186° |
| 229 | 1-(2-Chloro-6-fluorobenzoyl)-3-(6-(4-chlorophenylthio)-3-pyridinyl)urea | 148–150° |
| 230 | 1-(2,6-Dichlorobenzoyl)-3-(6-(2-chloro-5-(trifluoromethyl)phenoxy)-5-chloro-3-pyridinyl)urea | 204–207° |
| 231 | 1-(2,6-Dimethoxybenzoyl)-3-(6-(2-chloro-5-(trifluoromethyl)phenoxy)-5-chloro-3-pyridinyl)urea | 194–196° |
| 232 | 1-(2,6-Dichlorobenzoyl)-3-(6-(3,5-dichlorophenoxy)-5-chloro-3-pyridinyl)urea | 197–200° |
| 233 | 1-(2,6-Dimethoxybenzoyl)-3-(6-(3,5-dichlorophenoxy)-5-chloro-3-pyridinyl)urea | 196–199° |
| 234 | 1-(2,6-Dichlorobenzoyl)-3-(6-(2-chloro-5-(trifluoromethyl)phenoxy)-3-pyridinyl)urea | 187–191° |
| 235 | 1-(2,6-Dimethoxybenzoyl)-3-(6-(2-chloro-5-(trifluoromethyl)phenoxy)-3-pyridinyl)urea | 199–202° |
| 236 | 1-(2-Chloro-6-fluorobenzoyl)-3-(6-(4-chloro-3-(trifluoromethyl)phenoxy)-3-pyridinyl)urea | 179–185° |
| 237 | 1-(2,6-Difluorobenzoyl)-3-(6-(4-chloro-3-(trifluoromethyl)phenoxy)-3-pyridinyl)urea | 183–186° |
| 238 | 1-(2-Fluoro-6-methoxybenzoyl)-3-(6-(3-trifluoromethyl)phenoxy)-3-pyridinyl)urea | 146–148° |
| 239 | 1-(2-Fluoro-6-methoxybenzoyl)-3-(6-(2-chloro-5-(trifluoromethyl)phenoxy)-3-pyridinyl)urea | |
| 240 | 1-(2-Fluoro-6-methoxybenzoyl)-3-(6-(3,5-dichlorophenoxy)-3-pyridinyl)urea | 190–192° |
| 241 | 1-(2-Chloro-6-methoxybenzoyl)-3-(6-(4-chloro-3-(trifluoromethyl)phenoxy)-3-pyridinyl)urea | 164–166° |
| 242 | 1-(2-Chloro-6-methylbenzoyl)-3-(6-(3,5-dichlorophenoxy)-3-pyridinyl)urea | 193–196° |
| 243 | 1-(2-Chloro-6-methylbenzoyl)-3-(6-(2,4-dichlorobenzyloxy)-3-pyridinyl)urea | 190–193° |
| 244 | 1-(2-Chloro-6-methylbenzoyl)-3-(6-(3-(trifluoromethyl)phenoxy)-3-pyridinyl)urea | 156–158° |
| 245 | 1-(2-Chloro-6-methylbenzoyl)-3-(6-(2-chloro-5-(trifluoromethyl)phenoxy)-3-pyridinyl)urea | |
| 246 | 1-(2-Chloro-6-methylbenzoyl)-3-(6-(4-chlorophenylthio)-3-pyridinyl)urea | |
| 247 | 1-(2-Chloro-6-methylbenzoyl)-3-(6-(4-chlorophenylsulfonyl)-3-pyridinyl)urea | |
| 248 | 1-(2,6-Dichlorobenzoyl)-3-(5-(4-chlorophenylthio)-2-pyridinyl)urea | 132–135° |
| 249 | 1-(2,6-Dimethoxybenzoyl)-3-(5-(4-chlorophenylthio)-2-pyridinyl)urea | 85–87° |
| 250 | 1-(2-Chlorobenzoyl)-3-(5-(3-trifluoromethyl)phenylthio)-2-pyridinyl)urea | 194–197° |
| 251 | 1-(2-Chlorobenzoyl)-3-(5-(3-(trifluoromethyl)phenylthio)-2-pyridinyl)thiourea | 114–116° |
| 252 | 1-(2,6-Dichlorobenzoyl)-3-(5-(4-chlorobenzylthio)-2-pyridinyl)urea | 229–231° |
| 253 | 1-(2,6-Dimethoxybenzoyl)-3-(5-(4-chlorobenzylthio)-2-pyridinyl)urea | 164–167° |
| 254 | 1-(2,6-Dichlorobenzoyl)-3-(6-(3,5-dimethoxyphenoxy)-3-pyridinyl)urea | 160–163° |
| 255 | 1-(2,6-Dimethoxybenzoyl)-3-(6-(3,5-dimethoxyphenoxy)-3-pyridinyl)urea | |
| 256 | 1-(2,6-Difluorobenzoyl)-3-(6-(3,5-dimethoxyphenoxy)-3-pyridinyl)urea | |
| 257 | 1-(2-Chloro-6-methoxybenzoyl)-3-(6-(3,5-dimethoxyphenoxy)-3-pyridinyl)urea | |
| 258 | 1-(2-Fluoro-6-methoxybenzoyl)-3-(6-(3,5-dimethoxyphenoxy)-3-pyridinyl)urea | |
| 259 | 1-(2-Chloro-6-fluorobenzoyl)-3-(6-(3,5-dimethoxyphenoxy)-3-pyridinyl)urea | |
| 260 | 1-(2,6-Dichlorobenzoyl)-3-(6-(2-chloro-4-(trifluoromethyl)phenoxy)-3-pyridinyl)urea | |
| 261 | 1-(2,6-Dimethoxybenzoyl)-3-(6-(2-chloro-4-(trifluoromethyl)phenoxy)-3-pyridinyl)urea | |
| 262 | 1-(2,6-Difluorobenzoyl)-3-(6-(2-chloro-4-(trifluoromethyl)phenoxy)-3-pyridinyl)urea | |
| 263 | 1-(2-Chloro-6-fluorobenzoyl)-3-(6-(2-chloro-4-(trifluoromethyl)- | |

-continued

| Example No. | Compound Name | Melting Point (C.) |
|---|---|---|
| | phenoxy-3-pyridinyl)urea | |
| 264 | 1-(2-Chloro-6-methoxybenzoyl)-3-(6-(2-chloro-4-(trifluoromethyl)phenoxy)-3-pyridinyl)urea | |
| 265 | 1-(2-Fluoro-6-methoxybenzoyl)-3-(6-(2-chloro-4-(trifluoromethyl)phenoxy)-3-pyridinyl)urea | |
| 266 | 1-(2,6-Dichlorobenzoyl)-3-(6-(3,5-bis(trifluoromethyl)-phenoxy)-3-pyridinyl)urea | |
| 267 | 1-(2,6-Dimethoxybenzoyl)-3-(6-(3,5-bis(trifluoromethyl)-phenoxy)-3-pyridinyl)urea | |
| 268 | 1-(2,6-Difluorobenzoyl)-3-(6-(3,5-bis(trifluoromethyl)-phenoxy)-3-pyridinyl)urea | |
| 269 | 1-(2-Chloro-6-fluorobenzoyl)-3-(6-(3,5-bis(trifluoromethyl)-phenoxy)-3-pyridinyl)urea | |
| 270 | 1-(2-Chloro-6-methoxybenzoyl)-3-(6-(3,5-bis(trifluoromethyl)-phenoxy)-3-pyridinyl)urea | |
| 271 | 1-(2-Fluoro-6-methoxybenzoyl)-3-(6-(3,5-bis(trifluoromethyl)-phenoxy)-3-pyridinyl)urea | |
| 272 | 1-(2,6-Dichlorobenzoyl)-3-(6-(2-fluoro-5-(trifluoromethyl)-phenoxy)-3-pyridinyl)urea | |
| 273 | 1-(2,6-Dimethoxybenzoyl)-3-(6-(2-fluoro-5-(trifluoromethyl)-phenoxy)-3-pyridinyl)urea | |
| 274 | 1-(2,6-Difluorobenzoyl)-3-(6-(2-fluoro-5-(trifluoromethyl)-phenoxy)-3-pyridinyl)urea | |
| 275 | 1-(2-Chloro-6-fluorobenzoyl)-3-(6-(2-fluoro-5-(trifluoromethyl)phenoxy)-3-pyridinyl)urea | |
| 276 | 1-(2-Chloro-6-methoxybenzoyl)-3-(6-(2-fluoro-5-(trifluoromethyl)-phenoxy)-3-pyridinyl)urea | |
| 277 | 1-(2-Fluoro-6-methoxybenzoyl)-3-(6-(2-fluoro-5-(trifluoromethyl)-phenoxy)-3-pyridinyl)urea | |
| 278 | 1-(2,6-Dichlorobenzoyl)-3-(6-(3,5-bis(trifluoromethyl)benzyloxy)-3-pyridinyl)urea | |
| 279 | 1-(2,6-Dichlorobenzoyl)-3-(5-chloro-6-(4-chloro-3-(trifluoromethyl)-phenoxy)-3-pyridinyl)urea | |
| 280 | 1-(2,6-Dimethoxybenzoyl)-3-(6-(3,5-bis(trifluoromethyl)-benzyloxy)-3-pyridinyl)urea | |
| 281 | 1-(2,6-Difluorobenzoyl)-3-(6-(3,5-bis(trifluoromethyl)benzyloxy)-3-pyridinyl)urea | |
| 282 | 1-(2-Chloro-6-fluorobenzoyl)-3-(6-(3,5-bis(trifluoromethyl)-benzyloxy)-3-pyridinyl)urea | |
| 283 | 1-(2-Chloro-6-methoxybenzoyl)-3-(6-(3,5-bis(trifluoromethyl)-benzyloxy)-3-pyridinyl)urea | |
| 284 | 1-(2-Fluoro-6-methoxybenzoyl)-3-(6-(3,5-bis(trifluoromethyl)-benzyloxy)-3-pyridinyl)urea | |
| 285 | 1-(2,6-Dichlorobenzoyl)-3-(6-(2,3-dichlorophenoxy)-3-pyridinyl)urea | 217–219° |

The compounds of the present invention are useful for the control of insects of various orders, including Coleoptera such as Mexican bean beetle, boll weevil, corn rootworms, cereal leaf beetle, flea beetles, borers, Colorado potato beetle, grain beetles, alfalfa weevil, carpet beetle, confused flour beetle, powder post beetle, wireworms, rice weevil, rose beetle, plum curculio, white grubs; Diptera, such as house fly, yellow fever mosquito, stable fly, horn fly, blowfly, cabbage maggot, carrot rust fly; Lepidoptera, such as southern armyworm, codling moth, cutworm, clothes moth, Indian meal moth, leaf rollers, corn earworm, European corn borer, cabbage worm, cabbage looper, cotton bollworm, bagworm, eastern tent caterpillar, and webworm, fall armyworm; and Orthoptera, such as German cockroach and American cockroach.

The compounds of the present invention are additionally useful for the control of other insects such as common cattle grub, face fly, mosquitoes, spruce bud worm, bollworms, tabanid fly, tobacco budworm, armyworms including beet armyworm and yellow striped armyworm, Southwestern corn borer, potato leafhopper, lesser cornstalk borer, grasshoppers, cotton fleahopper, wheat stem sawfly, horse fly, webworms, maggots, velvetbean capterpillar, pecan weevil, whitefringed beetle, pecan nut casebearer, pink bollworm, darkling beetle, hickory shuckworm, walnut caterpillar, tobacco hornworm, loopers, Egyptian cotton leafworm, cockroaches, green cloverworm, alfalfa caterpillar, corn leaf beetle, leaf miner fly, diamondback moth, rednecked peanut worm, stalk borer, cigarette beetle, sunflower moth, tomato pinworm, oriental fruit moth, peachtree borer, melon fly, imported cabbage worm, lesser peachtree borer, grape root borer, black fly, pepper weevil, threestriped blister beetle, sunflower beetle, nose bot fly, grape berry moth, sheep ked, and leaf rollers.

It is believed that the present compounds act by interfering with the mechanism of metamorphosis which occurs in insects, causing the death of the insects. It is also believed that ingestion by the insects is necessary to invoke this mechanism. While the death of any given insect may be delayed until that insect reaches some stage of metamorphosis, the net result of this activity is the control and suppression of insects.

Therefore, in another embodiment, the present invention is directed to a method of suppressing insects which comprises applying to a locus of the insects an effective amount of a compound of the present invention. The locus can be any environment inhabited by insects to be controlled, such as soil, air, water, foods, vegetation, manure, inert objects, stored matter such as grain, and the like.

Preferably the compounds of the present invention are supplied in a formulation, for ease of application. The compounds can be formulated with various adjuvants, including water, organic liquids, surface-active agents, inert solids, and the like. Suitable surface-active agents include anionic agents, such as sodium lauryl sulfate, sodium dodecylbenzenesulfonate, and the like; and nonionic agents, such as polyethylene glycol p-nonylphenyl ether. Mixtures are often desirably employed. The formulation can take the form of a liquid, dust, granule, aerosol, etc. The formulation can be concentrated, as in a slow release formulation or as in a formulation to be diluted with water before application to the locus of insects. Many methods of formulation are known in the art and can be employed to implement the present invention.

The concentration of active agent in the formulation is not critical, inasmuch as an effective concentration will vary with the nature of the locus to be treated, the severity of insect infestation, the susceptibility of the particular insects involved, etc. In general, concentrations ranging from about 0.1 to 1000 ppm give good results. As exemplified by Table 2, below, lesser concentrations of from about 1 to about 100 ppm have given good control of southern armyworm.

The insecticidal activity of the present compounds was determined by testing the efficacy of formulations of the compounds against Mexican bean beetle larvae (*Epilachna varivestis*), and against southern armyworm larvae (*Spodoptera eridania*). These insects are members of the Coleoptera and Lepidoptera orders of insects, respectively. The formulations were applied to the foliage of plants and the larvae were subsequently permitted to feed on the foliage. The compounds were tested in a plurality of concentrations, from a concentration of about 1000 ppm. to about 1 ppm.

Each compound to be tested was formulated by dissolving 10 mg. of the compound in 1 ml. of a solvent made up with 23 grams of Toximul R and 13 grams of Toximul S per liter of 1:1 anhydrous ethanol and acetone. Each of Toximul R and Toximul S is a sulfonate/-nonionic blend produced by Stepan Chemical Company, Northfield, Ill. Water was then added to obtain 10 ml. of solution containing the compound in a concentration of 1000 parts per million. Alternatively, 11 mg. of compound was used, to make up 11 ml. of solution, of which 10 ml. was employed as a 1000 ppm. treating solution, and of which the remaining 1 ml. was diluted further with water to obtain a treating solution containing 100 ppm. of compound. Formulations of the compound at lesser concentrations were prepared in the same manner, using the same solvent.

Each solution of test compound was sprayed onto two 4-inch square pots of bean plants containing 6 to 10 plants per pot. The plants were allowed to dry and then 12 leaves were removed and the cut ends wrapped in water-soaked cellucotton. The leaves were divided between six 100×20 mm. plastic petri dishes. Five second-instar Mexican bean beetle larvae (*Epilachna varivestis*) and five second- and third-instar southern armyworm larvae (*Spodoptera eridania*) were placed in each of three dishes. The dishes were then placed in a room wherein the temperature and relative humidity were controlled at about 78° F. and about 51 percent, respectively, for a period of four days, at which time the first evaluation of the effects of the test compounds was made. After this evaluation, two fresh leaves from the original treated pots were placed in each dish. The dishes were again maintained in the temperature and humidity controlled room for an additional three days until the final seven-day evaluation was made.

Insecticidal effect was determined by counting the number of living larvae of each species, and applying the following rating code:
0 = all larvae living
1 = half or more than half of the larvae living
2 = less than half of the larvae living
3 = all larvae dead The results of this test are set forth in Table 1, which follows. In the table, column 1 identifies the compounds by the number of the preparative example; column 2 lists the concentration of the test compound in the formulation; and columns 3 through 6 give the rating code at days 4 and 7 for the two insects against which the compounds were tested.

TABLE 1

| Exmple No. | Appln. Rate ppm | Insect Control | | | |
|---|---|---|---|---|---|
| | | Mexican Bean Beetle | | Southern Armyworm | |
| | | 4 days | 7 days | 4 days | 7 days |
| 8 | 1000 | 1 | 3 | 2 | 3 |
| | 100 | 1 | 3 | 3 | 3 |
| 9 | 1000 | 3 | 3 | 3 | 3 |
| | 100 | 3 | 3 | 3 | 3 |
| 10 | 1000 | 2 | 3 | 1 | 3 |
| | 100 | 2 | 3 | 0 | 1 |
| 11 | 1000 | 2 | 3 | 3 | 3 |
| | 100 | 2 | 2 | 2 | 2 |
| 12 | 1000 | 2 | 2 | 3 | 3 |
| | 100 | 1 | 2 | 3 | 3 |
| 19 | 1000 | 2 | 3 | 3 | 3 |
| | 100 | 2 | 3 | 2 | 3 |
| 20 | 1000 | 2 | 3 | 3 | 3 |
| | 100 | 1 | 2 | 3 | 3 |
| 21 | 1000 | 2 | 3 | 3 | 3 |
| | 100 | 2 | 3 | 3 | 3 |
| 22 | 1000 | 2 | 2 | 2 | 3 |
| | 100 | 2 | 3 | 3 | 3 |
| 23 | 1000 | 2 | 2 | 3 | 3 |
| | 100 | 2 | 3 | 3 | 3 |
| 24 | 1000 | 2 | 3 | 1 | 2 |
| | 100 | 2 | 3 | 0 | 1 |
| 25 | 1000 | 3 | 3 | 3 | 3 |
| | 100 | 3 | 3 | 2 | 2 |
| 26 | 1000 | 2 | 2 | 3 | 3 |
| | 100 | 0 | 2 | 2 | 3 |
| 27 | 1000 | 2 | 3 | 3 | 3 |
| | 100 | 1 | 3 | 1 | 1 |
| 28 | 1000 | 2 | 2 | 3 | 3 |
| | 100 | 2 | 2 | 3 | 3 |
| 29 | 1000 | 3 | 3 | 3 | 3 |
| | 100 | 2 | 3 | 2 | 3 |
| 30 | 1000 | 2 | 3 | 3 | 3 |
| | 100 | 2 | 3 | 2 | 3 |
| 31 | 1000 | 2 | 3 | 2 | 3 |
| | 100 | 2 | 3 | 1 | 1 |
| 32 | 1000 | 1 | 3 | 0 | 0 |
| | 100 | 1 | 3 | 0 | 0 |
| 33 | 1000 | 1 | 3 | 0 | 0 |
| | 100 | 1 | 3 | 0 | 0 |
| 34 | 1000 | 2 | 3 | 3 | 3 |
| | 100 | 2 | 3 | 3 | 3 |
| 35 | 1000 | 2 | 3 | 1 | 3 |
| | 100 | 2 | 3 | 0 | 0 |
| 36 | 1000 | 2 | 3 | 2 | 2 |
| | 100 | 1 | 2 | 0 | 1 |
| 37 | 1000 | 2 | 3 | 0 | 0 |
| | 100 | 2 | 3 | 0 | 0 |
| 38 | 1000 | 2 | 3 | 0 | 0 |
| | 100 | 2 | 3 | 0 | 0 |
| 39 | 1000 | 1 | 2 | 3 | 3 |
| | 100 | 1 | 3 | 2 | 3 |
| 40 | 1000 | 3 | 3 | 3 | 3 |
| | 100 | 2 | 2 | 1 | 2 |
| 41 | 1000 | 2 | 3 | 3 | 3 |
| | 100 | 1 | 3 | 3 | 3 |
| 42 | 1000 | 3 | 3 | 0 | 0 |

TABLE 1-continued

| Example No. | Appln. Rate ppm | Insect Control Mexican Bean Beetle 4 days | 7 days | Southern Armyworm 4 days | 7 days |
|---|---|---|---|---|---|
|  | 100 | 1 | 3 | 0 | 0 |
| 43 | 1000 | 3 | 3 | 1 | 1 |
|  | 100 | 2 | 3 | 1 | 1 |
| 44 | 1000 | 3 | 3 | 0 | 0 |
|  | 100 | 2 | 3 | 0 | 0 |
| 45 | 1000 | 3 | 3 | 3 | 3 |
|  | 100 | 2 | 3 | 3 | 3 |
| 46 | 1000 | 3 | 3 | 0 | 0 |
|  | 100 | 1 | 2 | 0 | 0 |
| 47 | 1000 | 2 | 3 | 1 | 2 |
|  | 100 | 1 | 3 | 0 | 0 |
| 48 | 1000 | 1 | 2 | 0 | 0 |
|  | 100 | 0 | 0 | 0 | 0 |
| 49 | 1000 | 1 | 2 | 3 | 3 |
|  | 100 | 0 | 0 | 3 | 3 |
| 50 | 1000 | 2 | 3 | 3 | 3 |
|  | 100 | 1 | 3 | 3 | 3 |
| 51 | 1000 | 2 | 3 | 3 | 3 |
|  | 100 | 2 | 3 | 3 | 3 |
| 52 | 1000 | 1 | 3 | 3 | 3 |
|  | 100 | 1 | 2 | 3 | 3 |
| 53 | 1000 | 3 | 3 | 2 | 3 |
|  | 100 | 2 | 3 | 1 | 2 |
| 54 | 1000 | 1 | 3 | 3 | 3 |
|  | 100 | 0 | 1 | 3 | 3 |
| 55 | 1000 | 2 | 2 | 1 | 2 |
|  | 100 | 2 | 2 | 0 | 1 |
| 56 | 1000 | 3 | 3 | 1 | 1 |
|  | 100 | 3 | 3 | 0 | 0 |
| 57 | 1000 | 2 | 3 | 3 | 3 |
|  | 100 | 2 | 2 | 3 | 3 |
| 59 | 1000 | 1 | 3 | 3 | 3 |
|  | 100 | 0 | 2 | 3 | 3 |
| 60 | 1000 | 2 | 3 | 3 | 3 |
|  | 100 | 1 | 3 | 3 | 3 |
| 61 | 1000 | 3 | 3 | 3 | 3 |
|  | 100 | 2 | 3 | 3 | 3 |
| 62 | 1000 | 3 | 3 | 2 | 3 |
|  | 100 | 2 | 3 | 0 | 1 |
| 63 | 1000 | 3 | 3 | 3 | 3 |
|  | 100 | 3 | 3 | 2 | 3 |
| 64 | 1000 | 2 | 2 | 3 | 3 |
|  | 100 | 0 | 1 | 2 | 3 |
| 65 | 1000 | 1 | 2 | 3 | 3 |
|  | 100 | 0 | 2 | 2 | 3 |
| 66 | 1000 | 0 | 2 | 0 | 0 |
| 67 | 1000 | 2 | 2 | 2 | 2 |
| 68 | 1000 | NT | 3 | NT | 3 |
|  | 100 | " | 3 | " | 3 |
| 69 | 1000 | NT | 3 | NT | 3 |
|  | 100 | " | 3 | " | 3 |
| 70 | 1000 | 2 | 3 | 3 | 3 |
|  | 100 | 2 | 3 | 2 | 3 |
| 71 | 1000 | 1 | 3 | 3 | 3 |
|  | 100 | 0 | 0 | 3 | 3 |
| 72 | 1000 | 2 | 3 | 0 | 0 |
|  | 100 | 2 | 3 | 0 | 0 |
| 73 | 1000 | 2 | 2 | 2 | 3 |
|  | 100 | 1 | 2 | 1 | 3 |
| 74 | 1000 | NT | 3 | NT | 3 |
|  | 100 | " | 3 | " | 3 |
| 75 | 1000 | 3 | 3 | 3 | 3 |
|  | 100 | 1 | 2 | 3 | 3 |
| 76 | 1000 | 2 | 3 | 3 | 3 |
|  | 100 | 2 | 3 | 3 | 3 |
| 77 | 1000 | 2 | 3 | 3 | 3 |
|  | 100 | 1 | 2 | 2 | 3 |
| 78 | 1000 | 2 | 2 | 3 | 3 |
|  | 100 | 1 | 1 | 2 | 3 |
| 79 | 1000 | 2 | 3 | 3 | 3 |
|  | 100 | 2 | 2 | 2 | 2 |
| 80 | 1000 | 2 | 3 | 3 | 3 |
|  | 100 | 1 | 2 | 2 | 3 |
| 81 | 1000 | 2 | 3 | 3 | 3 |
|  | 100 | 1 | 3 | 2 | 2 |
| 82 | 1000 | 2 | 2 | 3 | 3 |
|  | 100 | 2 | 2 | 3 | 3 |
| 83 | 1000 | 2 | 3 | 3 | 3 |
|  | 100 | 1 | 2 | 2 | 2 |
| 84 | 1000 | 2 | 2 | 3 | 3 |
|  | 100 | 2 | 3 | 3 | 3 |
| 85 | 1000 | 2 | 2 | 3 | 3 |
|  | 100 | 1 | 2 | 3 | 3 |
| 86 | 1000 | 2 | 3 | 2 | 3 |
|  | 100 | 1 | 2 | 3 | 3 |
| 87 | 1000 | 1 | 3 | 3 | 3 |
|  | 100 | 1 | 1 | 3 | 3 |
| 88 | 1000 | 2 | 3 | 1 | 2 |
|  | 100 | 1 | 3 | 0 | 0 |
| 89 | 1000 | 2 | 3 | 3 | 3 |
|  | 100 | 1 | 2 | 2 | 3 |
| 90 | 1000 | 0 | 2 | 1 | 3 |
|  | 100 | 0 | 1 | 1 | 3 |
| 91 | 1000 | 0 | 2 | 2 | 3 |
|  | 100 | 0 | 1 | 1 | 2 |
| 92 | 1000 | 1 | 3 | 1 | 2 |
|  | 100 | 1 | 2 | 1 | 1 |
| 93 | 1000 | 1 | 2 | 0 | 0 |
|  | 100 | 1 | 1 | 0 | 0 |
| 94 | 1000 | 2 | 3 | 0 | 0 |
|  | 100 | 1 | 2 | 0 | 0 |
| 95 | 1000 | 0 | 2 | 3 | 3 |
|  | 100 | 0 | 1 | 0 | 2 |
| 96 | 1000 | 3 | 3 | 0 | 0 |
|  | 100 | 2 | 3 | 0 | 0 |
| 97 | 1000 | 2 | 3 | 2 | 3 |
|  | 100 | 2 | 3 | 1 | 3 |
| 98 | 1000 | 2 | 3 | 3 | 3 |
|  | 100 | 2 | 3 | 3 | 3 |
| 99 | 1000 | 2 | 2 | 3 | 3 |
|  | 100 | 1 | 2 | 2 | 3 |
| 100 | 1000 | 2 | 3 | 2 | 3 |
|  | 100 | 2 | 3 | 1 | 2 |
| 101 | 1000 | 1 | 2 | 3 | 3 |
|  | 100 | 0 | 1 | 2 | 3 |
| 102 | 1000 | 2 | 2 | 3 | 3 |
|  | 100 | 2 | 2 | 2 | 3 |
| 103 | 1000 | 2 | 3 | 0 | 0 |
|  | 100 | 2 | 3 | 0 | 0 |
| 104 | 1000 | 1 | 2 | 0 | 0 |
|  | 100 | 1 | 1 | 0 | 0 |
| 105 | 1000 | 1 | 3 | 1 | 2 |
|  | 100 | 0 | 2 | 0 | 0 |
| 106 | 1000 | 1 | 3 | 0 | 1 |
|  | 100 | 0 | 1 | 0 | 0 |
| 107 | 1000 | 1 | 3 | 0 | 0 |
|  | 100 | 0 | 2 | 0 | 0 |
| 108 | 1000 | 0 | 1 | 0 | 0 |
|  | 100 | 0 | 0 | 0 | 0 |
| 109 | 1000 | 3 | 3 | 0 | 0 |
|  | 100 | 0 | 3 | 0 | 0 |
| 110 | 1000 | 0 | 0 | 0 | 0 |
|  | 100 | 0 | 0 | 0 | 0 |
| 111 | 1000 | 3 | 3 | 0 | 0 |
|  | 100 | 1 | 1 | 0 | 0 |
| 112 | 1000 | 0 | 0 | 1 | 3 |
|  | 100 | 0 | 0 | 1 | 1 |
| 113 | 1000 | 0 | 1 | 0 | 0 |
|  | 100 | 0 | 1 | 0 | 0 |
| 114 | 1000 | 1 | 2 | 2 | 2 |
|  | 100 | 1 | 2 | 1 | 1 |
| 115 | 1000 | 1 | 2 | 0 | 0 |
|  | 100 | 1 | 2 | 0 | 0 |
| 116 | 1000 | 0 | 0 | 0 | 0 |
|  | 100 | 0 | 0 | 0 | 0 |
| 117 | 1000 | 1 | 2 | 2 | 2 |
|  | 100 | 0 | 1 | 1 | 2 |
| 118 | 1000 | 2 | 2 | 1 | 1 |
|  | 100 | 1 | 2 | 0 | 0 |
| 119 | 1000 | 3 | 3 | 0 | 0 |
|  | 100 | 1 | 1 | 0 | 0 |
| 120 | 1000 | 3 | 3 | 3 | 3 |
|  | 100 | 3 | 3 | 3 | 3 |
| 121 | 1000 | 2 | 3 | 1 | 1 |
|  | 100 | 2 | 3 | 0 | 0 |
| 122 | 1000 | 2 | 3 | 1 | 1 |

TABLE 1-continued

| Exmple No. | Appln. Rate ppm | Insect Control | | | |
|---|---|---|---|---|---|
| | | Mexican Bean Beetle | | Southern Armyworm | |
| | | 4 days | 7 days | 4 days | 7 days |
| | 100 | 1 | 2 | 0 | 0 |
| 123 | 1000 | 2 | 2 | 2 | 2 |
| | 100 | 1 | 2 | 1 | 2 |
| 125 | 1000 | 1 | 2 | 3 | 3 |
| | 100 | 1 | 2 | 2 | 2 |
| 126 | 1000 | 2 | 3 | 3 | 3 |
| | 100 | 1 | 2 | 3 | 3 |
| 129 | 1000 | 2 | 3 | 3 | 3 |
| | 100 | 1 | 3 | 3 | 3 |
| 130 | 1000 | 2 | 3 | 3 | 3 |
| | 100 | 1 | 3 | 2 | 3 |
| 134 | 1000 | 1 | 2 | 0 | 0 |
| | 100 | 0 | 0 | 0 | 0 |
| 136 | 1000 | 2 | 3 | 3 | 3 |
| | 100 | 2 | 2 | 3 | 3 |
| 138 | 1000 | 3 | 3 | 3 | 3 |
| | 100 | 2 | 3 | 2 | 3 |
| 143 | 1000 | N/T | N/T | 1 | 2 |
| | 100 | " | " | 0 | 0 |
| | 10 | " | " | 1 | 2 |
| 144 | 1000 | N/T | N/T | 3 | 3 |
| | 100 | " | " | 3 | 3 |
| | 10 | " | " | 1 | 2 |
| 155 | 1000 | " | " | 3 | 3 |
| | 100 | " | " | 1 | 2 |
| | 10 | " | " | 0 | 1 |
| 156 | 1000 | " | " | 2 | 2 |
| | 100 | " | " | 0 | 1 |
| | 10 | " | " | 0 | 0 |
| 199 | 1000 | " | " | 3 | 3 |
| | 100 | " | " | 3 | 3 |
| | 10 | " | " | 2 | 2 |
| 200 | 1000 | " | " | 3 | 3 |
| | 100 | " | " | 0 | 1 |
| | 10 | " | " | 0 | 0 |
| 202 | 1000 | " | " | 3 | 3 |
| | 100 | " | " | 0 | 2 |
| | 10 | " | " | 0 | 0 |
| 203 | 1000 | N/T | N/T | 3 | 3 |
| | 100 | " | " | 3 | 3 |
| | 10 | " | " | 1 | 2 |
| 204 | 1000 | " | " | 3 | 3 |
| | 100 | " | " | 3 | 3 |
| | 10 | " | " | 3 | 3 |
| 205 | 1000 | " | " | 3 | 3 |
| | 100 | " | " | 2 | 3 |
| | 10 | " | " | 1 | 2 |
| 208 | 1000 | " | " | 3 | 3 |
| | 100 | " | " | 1 | 2 |
| | 10 | " | " | 0 | 1 |
| 210 | 1000 | " | " | 3 | 3 |
| | 100 | " | " | 3 | 3 |
| | 10 | " | " | 1 | 3 |
| 212 | 1000 | " | " | 3 | 3 |
| | 100 | " | " | 0 | 0 |
| | 10 | " | " | 0 | 0 |
| 213 | 1000 | N/T | N/T | 3 | 3 |
| | 100 | " | " | 3 | 3 |
| | 10 | " | " | 2 | 3 |
| 214 | 1000 | " | " | 3 | 3 |
| | 100 | " | " | 3 | 3 |
| | 10 | " | " | 2 | 3 |
| 216 | 1000 | " | " | 3 | 3 |
| | 100 | " | " | 2 | 2 |
| | 10 | " | " | 1 | 1 |
| 217 | 1000 | " | " | 2 | 3 |
| | 100 | " | " | 0 | 0 |
| | 10 | " | " | 0 | 0 |
| 218 | 1000 | " | " | 3 | 3 |
| | 100 | " | " | 3 | 3 |
| | 10 | " | " | 0 | 0 |
| 219 | 1000 | " | " | 3 | 3 |
| | 100 | " | " | 3 | 3 |
| | 10 | " | " | 3 | 3 |
| 220 | 1000 | N/T | N/T | 3 | 3 |
| | 100 | " | " | 3 | 3 |
| | 10 | " | " | 3 | 3 |
| 221 | 1000 | " | " | 3 | 3 |
| | 100 | " | " | 3 | 3 |
| | 10 | " | " | 2 | 3 |
| 222 | 1000 | " | " | 3 | 3 |
| | 100 | " | " | 3 | 3 |
| | 10 | " | " | 2 | 3 |
| 223 | 1000 | " | " | 3 | 3 |
| | 100 | " | " | 3 | 3 |
| | 10 | " | " | 3 | 3 |
| 224 | 1000 | " | " | 3 | 3 |
| | 100 | " | " | 3 | 3 |
| | 10 | " | " | 2 | 3 |
| 225 | 1000 | " | " | 3 | 3 |
| | 100 | " | " | 3 | 3 |
| | 10 | " | " | 3 | 3 |
| 226 | 1000 | N/T | N/T | 3 | 3 |
| | 100 | " | " | 3 | 3 |
| | 10 | " | " | 3 | 3 |
| 227 | 1000 | " | " | 3 | 3 |
| | 100 | " | " | 3 | 3 |
| | 10 | " | " | 3 | 3 |
| 228 | 1000 | " | " | 3 | 3 |
| | 100 | " | " | 3 | 3 |
| | 10 | " | " | 3 | 3 |
| 229 | 1000 | " | " | 2 | 3 |
| | 100 | " | " | 2 | 3 |
| | 10 | " | " | 2 | 3 |
| 231 | 1000 | " | " | 3 | 3 |
| | 100 | " | " | 3 | 3 |
| | 10 | " | " | 1 | 3 |
| 248 | 1000 | 2 | 3 | 2 | 3 |
| | 100 | 2 | 2 | 3 | 3 |
| 249 | 1000 | 2 | 3 | 1 | 2 |
| | 100 | 1 | 3 | 0 | 0 |
| | 10 | 1 | 3 | 0 | 0 |
| 250 | 1000 | N/T | N/T | 1 | 2 |
| | 100 | " | " | 0 | 0 |
| | 10 | " | " | 0 | 0 |
| 251 | 1000 | " | " | 1 | 2 |
| | 100 | " | " | 0 | 1 |
| | 10 | " | " | 0 | 0 |
| 254 | 1000 | " | " | 2 | 3 |
| | 100 | " | " | 3 | 3 |
| | 10 | " | " | 1 | 3 |

Many of the compounds of the present invention were also tested in the same procedure described above but at lower concentrations. In these tests, percent control was determined by counting the number of living larvae per dish and using Abbott's formula [W. W. Abbott, "A Method of Computing the Effectiveness of an Insecticide", J. Econ. Entomol. 18, 265-7 (1925)]:

Percent Control =
$$\frac{\text{No. of survivors in control} - \text{No. of survivors in treatment} \times 100}{\text{No. survivors in control}}$$

The results are set forth in Tables 2A and 2B, which follow.

TABLE 2A

| | | Insect Control (%) | | | |
|---|---|---|---|---|---|
| | | Mexican Bean Beetle | | Southern Armyworm | |
| Example No. | Appln. Rate ppm. | 4 days | 7 days | 4 days | 7 days |
| 8 | 10 | 60 | 80 | 36 | 100 |
| | 25 | 80 | 100 | 100 | 100 |
| | 50 | 80 | 100 | 100 | 100 |
| | 100 | 80 | 100 | 100 | 100 |
| 8 | 1.0 | N/T | N/T | 13 | 33 |
| | 2.5 | " | " | 80 | 83 |
| | 5.0 | " | " | 93 | 92 |
| | 10. | " | " | 100 | 100 |

TABLE 2A-continued

| Example No. | Appln. Rate ppm. | Insect Control (%) | | | |
|---|---|---|---|---|---|
| | | Mexican Bean Beetle | | Southern Armyworm | |
| | | 4 days | 7 days | 4 days | 7 days |
| 9 | 10 | 71 | 100 | 29 | 77 |
| | 25 | 71 | 100 | 100 | 100 |
| | 50 | 86 | 100 | 100 | 100 |
| | 100 | 86 | 100 | 100 | 100 |
| 9 | 1.0 | 80 | 86 | N/T | N/T |
| | 2.5 | 87 | 100 | " | " |
| | 5.0 | 87 | 100 | " | " |
| | 10. | 93 | 100 | " | " |
| 10 | 10 | 0 | 13 | N/T | N/T |
| | 25 | 73 | 100 | " | " |
| | 50 | 80 | 100 | " | " |
| | 100 | 93 | 100 | " | " |
| 11 | 10 | 67 | 93 | 0 | 0 |
| | 25 | 93 | 100 | 0 | 0 |
| | 50 | 100 | 100 | 27 | 47 |
| | 100 | 100 | 100 | 53 | 86 |
| 11 | 1.0 | | 0 | N/T | N/T |
| | 2.5 | 0 | 0 | " | " |
| | 5. | 20 | 20 | " | " |
| | 10. | 40 | 47 | " | " |
| 19 | 10 | 47 | 67 | 73 | 100 |
| | 25 | 60 | 100 | 87 | 100 |
| | 50 | 80 | 100 | 93 | 100 |
| | 100 | 100 | 100 | 100 | 100 |
| 19 | 1.0 | N/T | N/T | 0 | 0 |
| | 2.5 | " | " | 0 | 40 |
| | 5. | " | " | 7 | 93 |
| | 10. | " | " | 40 | 100 |
| 20 | 10 | 73 | 100 | 13 | 13 |
| | 25 | 100 | 100 | 53 | 86 |
| | 50 | 93 | 100 | 73 | 93 |
| | 100 | 93 | 100 | 100 | 100 |
| 20 | 1.0 | 0 | 0 | N/T | N/T |
| | 2.5 | 0 | 53 | " | " |
| | 5. | 0 | 80 | " | " |
| | 10. | 33 | 100 | " | " |
| 21 | 10 | 80 | 100 | 80 | 100 |
| | 25 | 80 | 100 | 100 | 100 |
| | 50 | 93 | 100 | 100 | 100 |
| | 100 | 100 | 100 | 100 | 100 |
| 21 | 1.0 | 0 | 0 | 0 | 0 |
| | 2.5 | 0 | 7 | 0 | 28 |
| | 5. | 0 | 93 | 13 | 93 |
| | 10 | 20 | 100 | 80 | 100 |
| 22 | 10 | 40 | 53 | 67 | 100 |
| | 25 | 93 | 100 | 100 | 100 |
| | 50 | 87 | 100 | 100 | 100 |
| | 100 | 93 | 100 | 100 | 100 |
| 22 | 1.0 | N/T | N/T | 0 | 0 |
| | 2.5 | " | " | 7 | 7 |
| | 5. | " | " | 13 | 13 |
| | 10. | " | " | 40 | 100 |
| 23 | 10 | 100 | 100 | 13 | 53 |
| | 25 | 100 | 100 | 80 | 100 |
| | 50 | 100 | 100 | 93 | 100 |
| | 100 | 100 | 100 | 100 | 100 |
| 23 | 1.0 | 20 | 47 | N/T | N/T |
| | 2.5 | 67 | 100 | " | " |
| | 5. | 87 | 100 | " | " |
| | 10. | 87 | 100 | " | " |
| 24 | 10 | 93 | 100 | N/T | N/T |
| | 25 | 100 | 100 | " | " |
| | 50 | 100 | 100 | " | " |
| | 100 | 93 | 100 | " | " |
| 24 | 1.0 | 0 | 20 | N/T | N/T |
| | 2.5 | 27 | 27 | " | " |
| | 5. | 33 | 100 | " | " |
| | 10. | 67 | 100 | " | " |
| 25 | 10 | 13 | 33 | 0 | 0 |
| | 25 | 73 | 100 | 0 | 33 |
| | 50 | 60 | 100 | 13 | 40 |
| | 100 | 100 | 100 | 80 | 100 |
| 26 | 10 | 0 | 0 | 0 | 0 |
| | 25 | 0 | 67 | 0 | 0 |
| | 50 | 13 | 100 | 60 | 100 |
| | 100 | 28 | 100 | 100 | 100 |
| 27 | 10 | 0 | 33 | N/T | N/T |
| | 25 | 0 | 60 | " | " |
| | 50 | 27 | 100 | " | " |
| | 100 | 40 | 100 | " | " |
| 28 | 10 | N/T | N/T | 100 | 100 |
| | 25 | " | " | 100 | 100 |
| | 50 | " | " | 100 | 100 |
| | 100 | " | " | 100 | 100 |
| 28 | 1.0 | N/T | N/T | 0 | 0 |
| | 2.5 | " | " | 0 | 93 |
| | 5. | " | " | 0 | 93 |
| | 10. | " | " | 60 | 100 |
| 29 | 10 | 27 | 100 | 0 | 0 |
| | 25 | 33 | 100 | 7 | 33 |
| | 50 | 33 | 100 | 7 | 47 |
| | 100 | 40 | 100 | 73 | 86 |
| 29 | 1.0 | 0 | 0 | N/T | N/T |
| | 2.5 | 13 | 33 | " | " |
| | 5. | 27 | 72 | " | " |
| | 10. | 60 | 100 | " | " |
| 30 | 10 | 0 | 13 | 0 | 0 |
| | 25 | 13 | 87 | 0 | 27 |
| | 50 | 27 | 87 | 20 | 33 |
| | 100 | 40 | 100 | 33 | 100 |
| 31 | 10 | 7 | 7 | N/T | N/T |
| | 25 | 20 | 67 | " | " |
| | 50 | 40 | 80 | " | " |
| | 100 | 47 | 100 | " | " |
| 32 | 10 | 73 | 100 | N/T | N/T |
| | 25 | 80 | 100 | " | " |
| | 50 | 86 | 100 | " | " |
| | 100 | 93 | 100 | " | " |
| 32 | 1.0 | 0 | 13 | N/T | N/T |
| | 2.5 | 33 | 87 | " | " |
| | 5. | 53 | 93 | " | " |
| | 10. | 80 | 100 | " | " |
| 33 | 10 | 0 | 20 | N/T | N/T |
| | 25 | 0 | 87 | " | " |
| | 50 | 0 | 93 | " | " |
| | 100 | 40 | 100 | " | " |
| 34 | 10 | 0 | 100 | 40 | 53 |
| | 25 | 33 | 100 | 60 | 93 |
| | 50 | 73 | 100 | 67 | 100 |
| | 100 | 93 | 100 | 80 | 100 |
| 34 | 1.0 | 0 | 40 | N/T | N/T |
| | 2.5 | 7 | 100 | " | " |
| | 5. | 13 | 100 | " | " |
| | 10. | 27 | 100 | " | " |
| 35 | 10 | 27 | 100 | N/T | N/T |
| | 25 | 40 | 100 | " | " |
| | 50 | 60 | 100 | " | " |
| | 100 | 67 | 100 | " | " |
| 35 | 1.0 | 0 | 53 | N/T | N/T |
| | 2.5 | 47 | 87 | " | " |
| | 5. | 53 | 100 | " | " |
| | 10. | 73 | 100 | " | " |
| 37 | 10 | 0 | 0 | N/T | N/T |
| | 25 | 0 | 60 | " | " |
| | 50 | 20 | 100 | " | " |
| | 100 | 33 | 100 | " | " |
| 38 | 10 | 27 | 100 | N/T | N/T |
| | 25 | 33 | 100 | " | " |
| | 50 | 40 | 100 | " | " |
| | 100 | 67 | 100 | " | " |
| 38 | 1.0 | 0 | 0 | N/T | N/T |
| | 2.5 | 40 | 100 | " | " |
| | 5. | 60 | 100 | " | " |
| | 10 | 67 | 100 | " | " |
| 39 | 10 | 0 | 0 | 0 | 0 |
| | 25 | 0 | 100 | 36 | 7 |
| | 50 | 27 | 100 | 21 | 86 |
| | 100 | 80 | 100 | 64 | 100 |
| 41 | 10 | 73 | 100 | 60 | 100 |
| | 25 | 80 | 100 | 100 | 100 |
| | 50 | 86 | 100 | 100 | 100 |
| | 100 | 86 | 100 | 100 | 100 |
| 42 | 10 | 67 | 100 | N/T | N/T |
| | 25 | 73 | 100 | " | " |

TABLE 2A-continued

| Example No. | Appln. Rate ppm. | Mexican Bean Beetle 4 days | Mexican Bean Beetle 7 days | Southern Armyworm 4 days | Southern Armyworm 7 days |
|---|---|---|---|---|---|
|  | 50 | 73 | 100 | " | " |
|  | 100 | 86 | 100 | " | " |
| 50 | 10 | 13 | 67 | 67 | 100 |
|  | 25 | 80 | 93 | 100 | 100 |
|  | 50 | 86 | 93 | 100 | 100 |
|  | 100 | 93 | 93 | 100 | 100 |
| 63 | 10 | 0 | 53 | 100 | 100 |
|  | 25 | 67 | 86 | 100 | 100 |
|  | 50 | 73 | 93 | 100 | 100 |
|  | 100 | 100 | 100 | 100 | 100 |
| 65 | 10 | N/T | N/T | 27 | 93 |
|  | 25 | " | " | 80 | 100 |
|  | 50 | " | " | 86 | 100 |
|  | 100 | " | " | 100 | 100 |
| 65 | 1.0 | N/T | N/T | 0 | 0 |
|  | 2.5 | " | " | 7 | 7 |
|  | 5. | " | " | 13 | 47 |
|  | 10. | " | " | 27 | 100 |
| 66 | 10 | 0 | 0 | 0 | 0 |
|  | 50 | 0 | 7 | 0 | 0 |
|  | 100 | 0 | 100 | 0 | 0 |
| 67 | 10 | 40 | 67 | 0 | 0 |
|  | 50 | 60 | 100 | 0 | 0 |
|  | 100 | 93 | 100 | 0 | 0 |
| 68 | 10 | 60 | 73 | 40 | 73 |
|  | 50 | 73 | 80 | 100 | 100 |
|  | 100 | 80 | 100 | 100 | 100 |
| 68 | 1.0 | 0 | 0 | 0 | 0 |
|  | 2.5 | 7 | 33 | 7 | 13 |
|  | 5. | 20 | 47 | 13 | 33 |
|  | 10. | 53 | 100 | 27 | 86 |
| 69 | 10 | 0 | 0 | 0 | 0 |
|  | 50 | 20 | 73 | 53 | 93 |
|  | 100 | 80 | 100 | 93 | 100 |
| 70 | 10 | 0 | 73 | 7 | 7 |
|  | 25 | 60 | 93 | 47 | 80 |
|  | 50 | 67 | 100 | 67 | 100 |
|  | 100 | 73 | 100 | 73 | 100 |
| 70 | 1.0 | 0 | 0 | N/T | N/T |
|  | 2.5 | 13 | 27 | " | " |
|  | 5. | 33 | 40 | " | " |
|  | 10. | 40 | 100 | " | " |
| 71 | 10 | N/T | N/T | 47 | 87 |
|  | 25 | " | " | 100 | 100 |
|  | 50 | " | " | 100 | 100 |
|  | 100 | " | " | 100 | 100 |
| 71 | 1.0 | N/T | N/T | 0 | 0 |
|  | 2.5 | " | " | 7 | 47 |
|  | 5. | " | " | 27 | 86 |
|  | 10. | " | " | 47 | 100 |
| 71 | 1.0 | N/T | N/T | N/T | 0 |
|  | 2.5 | " | " | " | 21 |
|  | 5. | " | " | " | 64 |
|  | 10. | " | " | " | 100 |
| 72 | 10 | 27 | 100 | N/T | N/T |
|  | 25 | 33 | 100 | " | " |
|  | 50 | 40 | 100 | " | " |
|  | 100 | 87 | 100 | " | " |
| 72 | 1.0 | 33 | 53 | N/T | N/T |
|  | 2.5 | 73 | 100 | " | " |
|  | 5. | 86 | 100 | " | " |
|  | 10. | 100 | 100 | " | " |
| 73 | 10 | 7 | 27 | 0 | 0 |
|  | 25 | 40 | 67 | 7 | 53 |
|  | 50 | 67 | 100 | 47 | 100 |
|  | 100 | 73 | 100 | 100 | 100 |
| 74 | 10 | 27 | 93 | 100 | 100 |
|  | 50 | 47 | 100 | 100 | 100 |
|  | 100 | 53 | 100 | 100 | 100 |
| 74 | 1.0 | 0 | 7 | 0 | 0 |
|  | 2.5 | 27 | 53 | 7 | 47 |
|  | 5. | 33 | 93 | 27 | 73 |
|  | 10. | 53 | 100 | 60 | 93 |
| 75 | 10 | 0 | 13 | 33 | 47 |
|  | 25 | 7 | 40 | 80 | 100 |
|  | 50 | 27 | 47 | 100 | 100 |
|  | 100 | 53 | 93 | 100 | 100 |
| 76 | 10 | N/T | 100 | N/T | 0 |
|  | 25 | " | 100 | " | 71 |
|  | 50 | " | 72 | " | 93 |
|  | 100 | " | 100 | " | 100 |
| 76 | 1.0 | 0 | 20 | N/T | N/T |
|  | 2.5 | 87 | 86 | " | " |
|  | 5. | 87 | 93 | " | " |
|  | 10. | 93 | 100 | " | " |
| 77 | 10 | N/T | N/T | 0 | 0 |
|  | 25 | " | " | 13 | 27 |
|  | 50 | " | " | 33 | 53 |
|  | 100 | " | " | 60 | 80 |
| 78 | 10 | N/T | N/T | 0 | 0 |
|  | 25 | " | " | 20 | 100 |
|  | 50 | " | " | 27 | 100 |
|  | 100 | " | " | 87 | 100 |
| 79 | 10 | N/T | N/T | 0 | 0 |
|  | 25 | " | " | 0 | 0 |
|  | 50 | " | " | 13 | 33 |
|  | 100 | " | " | 47 | 86 |
| 80 | 10 | 7 | 27 | 33 | 100 |
|  | 25 | 33 | 93 | 100 | 100 |
|  | 50 | 67 | 100 | 100 | 100 |
|  | 100 | 80 | 100 | 100 | 100 |
| 80 | 1.0 | N/T | N/T | 0 | 0 |
|  | 2.5 | " | " | 7 | 40 |
|  | 5. | " | " | 7 | 60 |
|  | 10. | " | " | 27 | 93 |
| 81 | 10 | 0 | 33 | 0 | 0 |
|  | 25 | 7 | 53 | 27 | 67 |
|  | 50 | 27 | 100 | 87 | 100 |
|  | 100 | 73 | 100 | 87 | 100 |
| 82 | 10 | 100 | 100 | 100 | 100 |
|  | 25 | 100 | 100 | 100 | 100 |
|  | 50 | 100 | 100 | 100 | 100 |
|  | 100 | 100 | 100 | 100 | 100 |
| 82 | 1.0 | 73 | 100 | 0 | 0 |
|  | 2.5 | 100 | 100 | 27 | 93 |
|  | 5. | 100 | 100 | 33 | 93 |
|  | 10. | 100 | 100 | 87 | 100 |
| 82 | 0.1 | 0 | 0 | N/T | N/T |
|  | 0.25 | 53 | 93 | " | " |
|  | 0.5 | 72 | 100 | " | " |
|  | 1.0 | 80 | 100 | " | " |
|  | 10. | 100 | 100 | " | " |
| 83 | 10 | 100 | 100 | 80 | 100 |
|  | 25 | 100 | 100 | 100 | 100 |
|  | 50 | 100 | 100 | 100 | 100 |
|  | 100 | 100 | 100 | 100 | 100 |
| 83 | 1.0 | 0 | 7 | 0 | 0 |
|  | 2.5 | 20 | 33 | 7 | 67 |
|  | 5. | 20 | 40 | 33 | 93 |
|  | 10. | 87 | 93 | 33 | 100 |
| 84 | 10 | 93 | 100 | 93 | 100 |
|  | 25 | 93 | 100 | 100 | 100 |
|  | 50 | 100 | 100 | 100 | 100 |
|  | 100 | 100 | 100 | 100 | 100 |
| 84 | 1.0 | 13 | 47 | 0 | 27 |
|  | 2.5 | 86 | 100 | 60 | 93 |
|  | 5. | 93 | 100 | 93 | 100 |
|  | 10. | 100 | 100 | 100 | 100 |
| 85 | 10 | 7 | 33 | 47 | 80 |
|  | 25 | 53 | 86 | 100 | 100 |
|  | 50 | 67 | 86 | 100 | 100 |
|  | 100 | 93 | 100 | 100 | 100 |
| 86 | 10 | 7 | 53 | 13 | 20 |
|  | 25 | 33 | 86 | 33 | 100 |
|  | 50 | 73 | 86 | 93 | 100 |
|  | 100 | 86 | 93 | 100 | 100 |
| 87 | 10 | N/T | N/T | 20 | 86 |
|  | 25 | " | " | 100 | 100 |
|  | 50 | " | " | 100 | 100 |
|  | 100 | " | " | 100 | 100 |
| 87 | 1.0 | N/T | N/T | 0 | 13 |
|  | 2.5 | " | " | 53 | 93 |
|  | 5. | " | " | 80 | 100 |
|  | 10 | " | " | 100 | 100 |

TABLE 2A-continued

| Example No. | Appln. Rate ppm. | Insect Control (%) Mexican Bean Beetle | | Southern Armyworm | |
|---|---|---|---|---|---|
| | | 4 days | 7 days | 4 days | 7 days |
| 88 | 10 | 100 | 100 | N/T | N/T |
| | 25 | 93 | 100 | " | " |
| | 50 | 86 | 100 | " | " |
| | 100 | 100 | 100 | " | " |
| 88 | 1.0 | 27 | 53 | N/T | N/T |
| | 2.5 | 100 | 100 | " | " |
| | 5. | 100 | 100 | " | " |
| | 10. | 100 | 100 | " | " |
| 89 | 10 | 60 | 93 | 13 | 33 |
| | 25 | 86 | 100 | 100 | 100 |
| | 50 | 86 | 100 | 100 | 100 |
| | 100 | 93 | 100 | 100 | 100 |
| 90 | 10 | N/T | N/T | 0 | 53 |
| | 25 | " | " | 67 | 93 |
| | 50 | " | " | 100 | 100 |
| | 100 | " | " | 100 | 100 |
| 96 | 10 | 47 | 73 | N/T | N/T |
| | 25 | 53 | 100 | " | " |
| | 50 | 53 | 100 | " | " |
| | 100 | 100 | 100 | " | " |
| 97 | 10 | 86 | 100 | 0 | 72 |
| | 25 | 100 | 100 | 13 | 80 |
| | 50 | 100 | 100 | 33 | 93 |
| | 100 | 100 | 100 | 40 | 93 |
| 99 | 10 | 13 | 47 | 7 | 40 |
| | 25 | 67 | 93 | 33 | 100 |
| | 50 | 80 | 100 | 73 | 100 |
| | 100 | 86 | 100 | 93 | 100 |
| 101 | 10 | N/T | N/T | 13 | 40 |
| | 25 | " | " | 86 | 93 |
| | 50 | " | " | 100 | 100 |
| | 100 | " | " | 100 | 100 |
| 102 | 10 | N/T | N/T | 33 | 47 |
| | 25 | " | " | 93 | 100 |
| | 50 | " | " | 100 | 100 |
| | 100 | " | " | 100 | 100 |
| 103 | 10 | 0 | 100 | N/T | N/T |
| | 25 | 20 | 100 | " | " |
| | 50 | 27 | 100 | " | " |
| | 100 | 33 | 100 | " | " |
| 109 | 1.0 | N/T | N/T | 0 | 0 |
| | 2.5 | " | " | 7 | 13 |
| | 5. | " | " | 13 | 20 |
| | 10 | " | " | 20 | 73 |

TABLE 2B

| Example No. | Appln. Rate ppm. | Insect Control (%) Southern Armyworm | |
|---|---|---|---|
| | | 4 days | 7 days |
| 144 | 100 | 100 | 100 |
| | 50 | 53 | 72 |
| | 25 | 60 | 72 |
| | 10 | 13 | 20 |
| 199 | 100 | 100 | 100 |
| | 50 | 100 | 100 |
| | 25 | 100 | 100 |
| | 10 | 100 | 100 |
| 199 | 10 | 47 | 87 |
| | 5 | 0 | 53 |
| | 2.5 | 0 | 0 |
| | 1 | 0 | 0 |
| 203 | 100 | 100 | 100 |
| | 50 | 100 | 100 |
| | 25 | 100 | 100 |
| | 10 | 53 | 100 |
| 203 | 10 | 100 | 100 |
| | 5 | 27 | 53 |
| | 2.5 | 0 | 72 |
| | 1 | 0 | 0 |
| 204 | 100 | 100 | 100 |
| | 50 | 100 | 100 |
| | 25 | 100 | 100 |
| | 10 | 60 | 100 |
| 204 | 10 | 100 | 100 |

TABLE 2B-continued

| Example No. | Appln. Rate ppm. | Insect Control (%) Southern Armyworm | |
|---|---|---|---|
| | | 4 days | 7 days |
| | 5 | 100 | 100 |
| | 2.5 | 80 | 100 |
| | 1 | 60 | 87 |
| 205 | 100 | 100 | 100 |
| | 50 | 100 | 100 |
| | 25 | 72 | 100 |
| | 10 | 47 | 60 |
| 208 | 100 | — | 100 |
| | 50 | — | 100 |
| | 25 | — | 67 |
| | 10 | — | 7 |
| 210 | 100 | 100 | 100 |
| | 50 | 100 | 100 |
| | 25 | 100 | 100 |
| | 10 | 40 | 100 |
| 213 | 100 | 100 | 100 |
| | 50 | 100 | 100 |
| | 25 | 100 | 100 |
| | 10 | 100 | 100 |
| 213 | 10 | 100 | 100 |
| | 5 | 67 | 100 |
| | 2.5 | 53 | 100 |
| | 1 | 0 | 7 |
| 214 | 100 | 100 | 100 |
| | 50 | 100 | 100 |
| | 25 | 100 | 100 |
| | 10 | 100 | 100 |
| 214 | 10 | 100 | 100 |
| | 5 | 67 | 93 |
| | 2.5 | 0 | 47 |
| | 1 | 0 | 0 |
| 218 | 100 | 100 | 100 |
| | 50 | 100 | 100 |
| | 25 | 100 | 100 |
| | 10 | 80 | 80 |
| 218 | 10 | 100 | 100 |
| | 5 | 100 | 100 |
| | 2.5 | 100 | 100 |
| | 1 | 60 | 93 |
| 219 | 100 | 100 | 100 |
| | 50 | 100 | 100 |
| | 25 | 100 | 100 |
| | 10 | 100 | 100 |
| 219 | 10 | 100 | 100 |
| | 5 | 100 | 100 |
| | 2.5 | 100 | 100 |
| | 1 | 13 | 40 |
| 220 | 100 | 100 | 100 |
| | 50 | 100 | 100 |
| | 25 | 100 | 100 |
| | 10 | 100 | 100 |
| 220 | 10 | 100 | 100 |
| | 5 | 100 | 100 |
| | 2.5 | 80 | 100 |
| | 1 | 13 | 53 |
| 221 | 100 | 100 | 100 |
| | 50 | 100 | 100 |
| | 25 | 100 | 100 |
| | 10 | 100 | 100 |
| 221 | 10 | 72 | 100 |
| | 5 | 87 | 100 |
| | 2.5 | 80 | 100 |
| | 1 | 20 | 53 |
| 221 | 1 | 7 | 33 |
| | .5 | 0 | 27 |
| | .25 | 0 | 0 |
| | .125 | 0 | 0 |
| 222 | 100 | 100 | 100 |
| | 50 | 100 | 100 |
| | 25 | 100 | 100 |
| | 10 | 100 | 100 |
| 222 | 10 | 100 | 100 |
| | 5 | 93 | 100 |
| | 2.5 | 87 | 100 |
| | 1 | 72 | 100 |
| 222 | 1 | 60 | 93 |
| | .5 | 33 | 47 |
| | .25 | 7 | 7 |

TABLE 2B-continued

| Example No. | Appln. Rate ppm. | Insect Control (%) Southern Armyworm | |
|---|---|---|---|
| | | 4 days | 7 days |
| | .125 | 0 | 0 |
| 223 | 100 | 100 | 100 |
| | 50 | 100 | 100 |
| | 25 | 100 | 100 |
| | 10 | 100 | 100 |
| 223 | 10 | 80 | 93 |
| | 5 | 53 | 93 |
| | 2.5 | 47 | 100 |
| | 1 | 20 | 33 |
| 223 | 1 | 53 | 67 |
| | .5 | 0 | 13 |
| | .25 | 0 | 0 |
| | .125 | 0 | 0 |
| 224 | 100 | 100 | 100 |
| | 50 | 100 | 100 |
| | 25 | 100 | 100 |
| | 10 | 72 | 100 |
| 224 | 10 | 13 | 100 |
| | 5 | 0 | 53 |
| | 2.5 | 0 | 0 |
| | 1 | 0 | 0 |
| 225 | 100 | 100 | 100 |
| | 50 | 93 | 100 |
| | 25 | 93 | 100 |
| | 10 | 93 | 100 |
| 226 | 100 | 100 | 100 |
| | 50 | 100 | 100 |
| | 25 | 100 | 100 |
| | 10 | 100 | 100 |
| 227 | 100 | 100 | 100 |
| | 50 | 100 | 100 |
| | 25 | 100 | 100 |
| | 10 | 87 | 93 |
| 228 | 100 | 100 | 100 |
| | 50 | 100 | 100 |
| | 25 | 100 | 100 |
| | 10 | 100 | 100 |
| 228 | 10 | 100 | 100 |
| | 5 | 100 | 100 |
| | 2.5 | 100 | 100 |
| | 1 | 100 | 100 |
| 229 | 100 | 100 | 100 |
| | 50 | 100 | 100 |
| | 25 | 100 | 100 |
| | 10 | 100 | 100 |
| 248 | 100 | 100 | 100 |
| | 50 | 100 | 100 |
| | 25 | 100 | 100 |
| | 10 | 0 | 100 |
| 248 | 10 | 67 | 100 |
| | 5 | 0 | 60 |
| | 2.5 | 0 | 47 |
| | 1 | 0 | 0 |
| 254 | 100 | 100 | 100 |
| | 50 | 100 | 100 |
| | 25 | 100 | 100 |
| | 10 | 87 | 100 |
| 254 | 10 | 20 | 80 |
| | 5 | 0 | 33 |
| | 2.5 | 0 | 0 |
| | 1 | 0 | 0 |

Compounds of the present invention were also evaluated for the control of housefly (*Musca domestica*). In this evaluation, 3 mg. of each test compound was dissolved in 3 ml. of the same solvent described above for the evaluation against Mexican bean beetle and southern armyworm. Water was added to the solution, to a total volume of 30 ml. This provided a 100 ppm. solution. A 1 ml. portion of the 100 ppm. solution was diluted with 9 ml. of water to provide a 10 ppm. solution. A 5 ml. portion of each concentration solution was mixed with 250 grams of an artificial diet for housefly larvae to provide final concentrations of 2 ppm. and 1 ppm. Two replications were used for each concentration. Each treated diet was placed in a jar with 25 fresh housefly eggs on a filter paper, the top of the jar was covered with a paper towel rubber banded to the rim of the jar, and the jar was maintained for seven days at 78° F. and 45 percent relative humidity. Housefly pupae were then collected and the percent control of the pupae, compared to the pupae in the control, were determined for each treatment. The pupae were then maintained at room temperature for another week, and the percent control of the adult flies, compared to the adult flies in the control, was similarly determined. Results were as follows.

TABLE 3

| Example No. | Appln. Rate ppm. | Housefly Control (%) | |
|---|---|---|---|
| | | Pupae (7 days) | Adult flies (14 days) |
| 129 | 2 | 54 | 100 |
| | 1 | 42 | 90 |
| 136 | 2 | 18 | 82 |
| | 1 | 22 | 48 |
| 204 | 2 | 8 | 94 |
| 205 | 2 | 0 | 66 |
| 218 | 2 | 0 | 50 |
| | 1 | 0 | 42 |
| 220 | 2 | 62 | 80 |
| | 1 | 52 | 64 |
| 221 | 2 | 6 | 78 |
| | 1 | 0 | 60 |
| 222 | 2 | 92 | 100 |
| | 1 | 64 | 100 |
| 226 | 2 | 46 | 74 |
| | 1 | 10 | 22 |
| 227 | 2 | 88 | 98 |
| | 1 | 0 | 56 |

We claim:
1. Compound of the formula

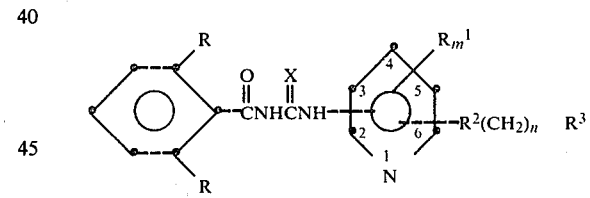

wherein each R is independently chloro, fluoro, methyl, or methoxy, with the proviso that when n is 0, one R is chloro, and $R^3$ is 3-(trifluoromethyl)-phenyl or 2-chloro-5-(trifluoromethyl)phenyl, the other R can additionally represent hydrogen; X is oxygen or sulfur; $R^1$ is chloro, methyl, or ethyl;

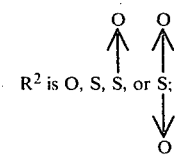

each of m and n is independently 0 or 1; $R^2$ is
(1) when n=1, phenyl or substituted phenyl, and
(2) when n=0, substituted phenyl, in either instance, substituted phenyl being (a) 3,5-dimethylphenyl or
(b) a radical of the formula

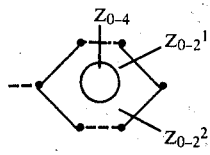

wherein each Z independently represents
(1) Br,
(2) Cl, or
(3) F;
$Z^1$ represents
(1) $CF_3$,
(2) $OCF_3$,
(3) $OC_2F_5$, or
(4) $OCF_2CF_2H$; and
$Z^2$ represents
(1) methyl,
(2) ethyl, or
(3) methoxy;
with the further limitation that the entire substituted phenyl radical bears
(1) at least one Z or $Z^1$,
(2) not more than 4 substituents, when all substituents are halo substituents;
(3) not more than 3 substituents, when any one substituent is other than halo; and
(4) not more than 2 different substituents;
and wherein positions on the pyridine ring are as follows:
(1) the nitrogen to pyridine bond is at the 2-position of the pyridine ring, the $-R^2-(CH_2)_n-R^3$ group is at the 5-position of the pyridine ring, and any $R^1$ is at the 4- or 6-position of the pyridine ring; or
(2) the nitrogen to pyridine bond is at the 3-position of the pyridine ring, the $-R^2-(CH_2)_n-R^3$ group is at the 6-position of the pyridine ring, and any $R^1$ is at the 5-position of the pyridine ring;
or an acid addition salt or N-oxide thereof.

2. The compound of claim 1 wherein:
(1) R in both occurrences is the same moiety and is chloro, fluoro, or methoxy;
(2) X represents oxygen;
(3) $R^2$ represents O or S;
(4) the nitrogen to pyridine bond is at the 3-position of the pyridine ring, the $-R^2-(CH_2)_n-R^3$ group is at the 6-position and any $R^1$ is at the 5-position; and
(5) in the formula $-R^2-(CH_2)_n-R^3$, $R^3$ is
phenyl (when n=1),
3-bromophenyl,
4-bromophenyl,
3-chlorophenyl,
4-chlorophenyl,
2,4-dichlorophenyl,
2,5-dichlorophenyl,
3,4-dichlorophenyl,
3,5-dichlorophenyl,
3-(trifluoromethyl)phenyl,
4-(trifluoromethyl)phenyl,
3,5-bis(trifluoromethyl)phenyl,
3-(trifluoromethyl)-4-chlorophenyl,
4-(trifluoromethyl)-3-chlorophenyl,
4-fluorophenyl,
2,3,5,6-tetrafluorophenyl,
3-methyl-4-chlorophenyl,
3-methyl-4-bromophenyl, or
2-chloro-5-(trifluoromethyl)phenyl.

3. The compound of claim 2 which is 1-(2,6-dimethoxybenzoyl)-3-(6-(4-chlorophenoxy)-3-pyridinyl)urea.

4. The compound of claim 2 which is 1-(2,6-dichlorobenzoyl)-3-(6-(4-chlorophenylthio)-3-pyridinyl)urea.

5. The compound of claim 2 which is 1-(2,6-dimethoxybenzoyl)-3-(6-(4-chlorophenylthio)-3-pyridinyl)urea.

6. The compound of claim 2 which is 1-(2,6-dimethoxybenzoyl)-3-(6-(4-chlorobenzylthio)-3-pyridinyl)urea.

7. The compound of claim 2 which is 1-(2,6-dichlorobenzoyl)-3-(6-(4-chlorophenylsulfonyl)-3-pyridinyl)urea.

8. The compound of claim 2 which is 1-(2,6-dichlorobenzoyl)-3-(5-methyl-6-(4-chlorophenylthio)-3-pyridinyl)urea.

9. The compound of claim 2 which is 1-(2,6-dichlorobenzoyl)-3-(5-methyl-6-(4-chlorophenylsulfonyl)-3-pyridinyl)urea.

10. The compound of claim 2 which is 1-(2,6-dimethoxybenzoyl)-3-(6-(4-chlorobenzyloxy)-3-pyridinyl)urea.

11. The compound of claim 2 which is 1-(2,6-dimethoxybenzoyl)-3-(6-(2,4-dichlorophenoxy)-3-pyridinyl)urea.

12. The compound of claim 2 which is 1-(2,6-dimethoxybenzoyl)-3-(6-(2,4-dichlorobenzylthio)-3-pyridinyl)urea.

13. The compound of claim 2 which is 1-(2,6-dimethoxybenzoyl)-3-(6-(3-chlorophenoxy)-3-pyridinyl)urea.

14. The compound of claim 2 which is 1-(2,6-dichlorobenzoyl)-3-(6-(3,5-dichlorophenoxy)-3-pyridinyl)urea.

15. The compound of claim 2 which is 1-(2,6-dimethoxybenzoyl-3-(6-(3,5-dichlorophenoxy)-3-pyridinyl)urea.

16. The compound of claim 2 which is 1-(2,6-dichlorobenzoyl)-3-(6-(3,4-dichlorophenylthio)-3-pyridinyl)urea.

17. The compound of claim 2 which is 1-(2,6-dimethoxybenzoyl)-3-(6-(3,4-dichlorophenylthio)-3-pyridinyl)urea.

18. The compound of claim 2 which is 1-(2,6-dimethoxybenzoyl)-3-(6-(3,4-dichlorophenoxy)-3-pyridinyl)urea.

19. The compound of claim 2 which is 1-(2,6-dimethoxybenzoyl)-3-(6-(3-methyl-4-chlorophenoxy)-3-pyridinyl)urea.

20. The compound of claim 2 which is 1-(2,6-dichlorobenzoyl)-3-(6-(2,3,5,6-tetrafluorophenylthio)-3-pyridinyl)urea.

21. The compound of claim 2 which is 1-(2,6-dimethoxybenzoyl)-3-(6-(2,3,5,6-tetrafluorophenylthio)-3-pyridinyl)urea.

22. The compound of claim 2 which is 1-(2,6-dichlorobenzoyl)-3-(6-(3-bromophenylthio)-3-pyridinyl)urea.

23. The compound of claim 2 which is 1-(2,6-dichlorobenzoyl)-3-(6-(4-bromophenylthio)-3-pyridinyl)urea.

24. The compound of claim 2 which is 1-(2,6-dimethoxybenzoyl)-3-(6-(4-bromophenylthio)-3-pyridinyl)urea.

25. The compound of claim 2 which is 1-(2,6-dichlorobenzoyl)-3-(6-(3-(trifluoromethyl)-phenylthio)-3-pyridinyl)urea.

26. The compound of claim 2 which is 1-(2,6-dimethoxybenzoyl)-3-(6-(3-(trifluoromethyl)-phenylthio)-3-pyridinyl)urea.

27. The compound of claim 2 which is 1-(2,6-dichlorobenzoyl)-3-(5-methyl-6-(3-(trifluoromethyl)-phenylthio)-3-pyridinyl)urea.

28. The compound of claim 2 which is 1-(2,6-dichlorobenzoyl)-3-(6-(3-(trifluoromethyl)-phenoxy)-3-pyridinyl)urea.

29. The compound of claim 2 which is 1-(2,6-dimethoxybenzoyl)-3-(6-(3-(trifluoromethyl)-phenoxy)-3-pyridinyl)urea.

30. The compound of claim 2 which is 1-(2,6-dimethoxybenzoyl)-3-(6-(2-chloro-5-(trifluoromethyl)-phenoxy)-3-pyridinyl)urea.

31. The compound of claim 2 which is 1-(2,6-dimethoxybenzoyl)-3-(6-benzylthio-3-pyridinyl)urea.

32. The compound of claim 2 which is 1-(2,6-dimethoxybenzoyl)-3-(6-benzyloxy-3-pyridinyl)urea.

33. The compound of claim 2 which is 1-(2,6-difluorobenzoyl)-3-(6-(4-chlorophenylthio)-3-pyridinyl)urea.

34. The compound of claim 2 which is 1-(2,6-difluorobenzoyl)-3-(6-(4-chlorophenoxy)-3-pyridinyl)urea.

35. The compound of claim 2 which is 1-(2,6-difluorobenzoyl)-3-(6-(3-(trifluoromethyl)-phenylthio)-3-pyridinyl)urea.

36. The compound of claim 2 which is 1-(2,6-difluorobenzoyl)-3-(6-(3-(trifluoromethyl)-phenoxy)-3-pyridinyl)urea.

37. The compound of claim 2 which is 1-(2,6-dichlorobenzoyl)-3-(6-(3,5-bis(trifluoromethyl)phenylthio)-3-pyridinyl)urea.

38. The compound of claim 2 which is 1-(2,6-dimethoxybenzoyl)-3-(6-(3,5-bis(trifluoromethyl)phenylthio)-3-pyridinyl)urea.

39. The compound of claim 2 which is 1-(2,6-dichlorobenzoyl)-3-(6-(3,5-bis(trifluoromethyl)phenoxy)-3-pyridinyl)urea.

40. The compound of claim 2 which is 1-(2,6-dimethoxybenzoyl)-3-(6-(3,5-bis(trifluoromethyl)phenoxy)-3-pyridinyl)urea.

41. The compound of claim 2 which is 1-(2,6-dichlorobenzoyl)-3-(6-(3-chloro-4-(trifluoromethyl)-phenylthio)-3-pyridinyl)urea.

42. The compound of claim 2 which is 1-(2,6-dimethoxybenzoyl)-3-(6-(3-chloro-4-(trifluoromethyl)-phenylthio)-3-pyridinyl)urea.

43. The compound of claim 2 which is 1-(2,6-dichlorobenzoyl)-3-(6-(3-(trifluoromethyl)-4-chlorophenylthio)-3-pyridinyl)urea.

44. The compound of claim 2 which is 1-(2,6-dimethoxybenzoyl)-3-(6-(3-(trifluoromethyl)-4-chlorophenylthio)-3-pyridinyl)urea.

45. The compound of claim 2 which is 1-(2,6-dichlorobenzoyl)-3-(6-(3,5-dichlorophenylthio)-3-pyridinyl)urea.

46. The compound of claim 2 which is 1-(2,6-dimethoxybenzoyl)-3-(6-(3,5-dichlorophenylthio)-3-pyridinyl)urea.

47. Method of suppressing insects of an order selected from the group consisting of Coleoptera, Diptera, Lepidoptera, and Orthoptera, which comprises applying to the locus of the insects an effective amount of an active agent which is a compound of claim 1.

48. The method of claim 47 in which the active agent is 1-(2,6-dimethoxybenzoyl)-3-(6-(4-chlorophenylthio)-3-pyridinyl)urea.

49. The method of claim 47 in which the active agent is 1-(2,6-dimethoxybenzoyl)-3-(6-benzylthio-3-pyridinyl)urea.

50. The method of claim 47 in which the active agent is 1-(2,6-dimethoxybenzoyl)-3-(6-(3,4-dichlorophenylthio)-3-pyridinyl)urea.

51. The method of claim 47 in which the active agent is 1-(2,6-dichlorobenzoyl)-3-(6-(3-(trifluoromethyl)-phenoxy)-3-pyridinyl)urea.

52. The method of claim 47 in which the active agent is 1-(2,6-dichlorobenzoyl)-3-(6-(3,4-dichlorophenylthio)-3-pyridinyl)urea.

53. The method of claim 47 in which the active agent is 1-(2,6-dichlorobenzoyl)-3-(6-(4-chlorophenylthio)-3-pyridinyl)urea.

54. The method of claim 47 in which the active agent is 1-(2,6-dichlorobenzoyl)-3-(6-(3-(trifluoromethyl)-phenylthio)-3-pyridinyl)urea.

55. The method of claim 47 in which the active agent is 1-(2,6-dimethoxybenzoyl)-3-(6-(3,5-dichlorophenoxy)-3-pyridinyl)urea.

56. Composition comprising a surface active agent and an insecticidally effective amount of an active agent which is a compound of claim 1.

57. The composition of claim 56 in which the active agent is 1-(2,6-dimethoxybenzoyl)-3-(6-(4-chlorophenylthio)-3-pyridinyl)urea.

58. The composition of claim 56 in which the active agent is 1-(2,6-dimethoxybenzoyl)-3-(6-benzylthio-3-pyridinyl)urea.

59. The composition of claim 56 in which the active agent is 1-(2,6-dimethoxybenzoyl)-3-(6-(3,4-dichlorophenylthio)-3-pyridinyl)urea.

60. The composition of claim 56 in which the active agent is 1-(2,6-dichlorobenzoyl)-3-(6-(3-(trifluoromethyl)phenoxy)-3-pyridinyl)urea.

61. The composition of claim 56 in which the active agent is 1-(2,6-dichlorobenzoyl)-3-(6-(3,4-dichlorophenylthio)-3-pyridinyl)urea.

62. The composition of claim 56 in which the active agent is 1-(2,6-dichlorobenzoyl)-3-(6-(4-chlorophenylthio)-3-pyridinyl)urea.

63. The composition of claim 56 in which the active agent is 1-(2,6-dichlorobenzoyl)-3-(6-(3-(trifluoromethyl)phenylthio)-3-pyridinyl)urea.

64. The composition of claim 56 in which the active agent is 1-(2,6-dimethoxybenzoyl)-3-(6-(3,5-dichlorophenoxy)-3-pyridinyl)urea.

65. The compound of claim 2 which is 1-(2,6-difluorobenzoyl)-3-(6-(3,5-dichlorophenoxy)-3-pyridinyl)urea.

66. The compound of claim 2 which is 1-(2-chloro-6-methoxybenzoyl)-3-(6-(3,5-dichlorophenoxy)-3-pyridinyl)urea.

67. The compound of claim 2 which is 1-(2-fluoro-6-methoxybenzoyl)-3-(6-(3,5-dichlorophenoxy)-3-pyridinyl)urea.

68. The compound of claim 2 which is 1-(2-chlorio-6-fluorobenzoyl)-3-(6-(3,5-dichlorophenoxy)-3-pyridinyl)urea.

69. The compound of claim 2 which is 1-(2,6-dichlorobenzoyl)-3-(6-(2-chloro-5-(trifluoromethyl)-phenoxy)-3-pyridinyl)urea.

70. The compound of claim 2 which is 1-(2,6-difluorobenzoyl)-3-(6-(2-chloro-5-(trifluoromethyl)-phenoxy)-3-pyridinyl)urea.

71. The compound of claim 2 which is 1-(2-chloro-6-methoxybenzoyl)-3-(6-(2-chloro-5-(trifluoromethyl)-phenoxy)-3-pyridinyl)urea.

72. The compound of claim 2 which is 1-(2-fluoro-6-methoxybenzoyl)-3-(6-(2-chloro-5-(trifluoromethyl)-phenoxy)-3-pyridinyl)urea.

73. The compound of claim 2 which is 1-(2-chloro-6-fluorobenzoyl)-3-(6-(2-chloro-5-(trifluoromethyl)-phenoxy)-3-pyridinyl)urea.

74. The compound of claim 2 which is 1-(2-chloro-6-methoxybenzoyl)-3-(6-(3-(trifluoromethyl)phenoxy)-3-pyridinyl)urea.

75. The compound of claim 2 which is 1-(2-fluoro-6-methoxybenzoyl)-3-(6-(3-(trifluoromethyl)phenoxy)-3-pyridinyl)urea.

76. The compound of claim 2 which is 1-(2-chloro-6-fluorobenzoyl)-3-(6-(3-(trifluoromethyl)phenoxy)-3-pyridinyl)urea.

77. The compound of claim 2 which is 1-(2,6-dichlorobenzoyl)-3-(6-(2,4-dichlorobenzyloxy)-3-pyridinyl)urea.

78. The compound of claim 2 which is 1-(2,6-dimethoxybenzoyl)-3-(6-(2,4-dichlorobenzyloxy)-3-pyridinyl)urea.

79. The compound of claim 2 which is 1-(2,6-difluorobenzoyl)-3-(6-(2,4-dichlorobenzyloxy)-3-pyridinyl)urea.

80. The compound of claim 2 which is 1-(2-chloro-6-methoxybenzoyl)-3-(6-(2,4-dichlorobenzyloxy)-3-pyridinyl)urea.

81. The compound of claim 2 which is 1-(2-fluoro-6-methoxybenzoyl)-3-(6-(2,4-dichlorobenzyloxy)-3-pyridinyl)urea.

82. The compound of claim 2 which is 1-(2-chloro-6-fluorobenzoyl)-3-(6-(2,4-dichlorobenzyloxy)-3-pyridinyl)urea.

83. The compound of claim 2 which is 1-(2,6-dichlorobenzoyl)-3-(6-(4-chloro-3-(trifluoromethyl)-phenoxy)-3-pyridinyl)urea.

84. The compound of claim 2 which is 1-(2,6-dimethoxybenzoyl)-3-(6-(4-chloro-3-(trifluoromethyl)-phenoxy)-3-pyridinyl)urea.

85. The compound of claim 2 which is 1-(2,6-difluorobenzoyl)-3-(6-(4-chloro-3-(trifluoromethyl)-phenoxy)-3-pyridinyl)urea.

86. The compound of claim 2 which is 1-(2-chloro-6-methoxybenzoyl)-3-(6-(4-chloro-3-(trifluoromethyl)-phenoxy)-3-pyridinyl)urea.

87. The compound of claim 2 which is 1-(2-fluoro-6-methoxybenzoyl)-3-(6-(4-chloro-3-(trifluoromethyl)-phenoxy)-3-pyridinyl)urea.

88. The compound of claim 2 which is 1-(2-chloro-6-fluorobenzoyl)-3-(6-(4-chloro-3-(trifluoromethyl)-phenoxy)-3-pyridinyl)urea.

89. The compound of claim 2 which is 1-(2,6-dichlorobenzoyl)-3-(5-chloro-6-(3-(trifluoromethyl)-phenoxy)-3-pyridinyl)urea.

90. The method of claim 47 wherein the active agent is 1-(2,6-dichlorobenzoyl)-3-(6-(3,5-dichlorophenoxy)-3-pyridinyl)urea.

91. The method of claim 47 in which the active agent is 1-(2,6-difluorobenzoyl)-3-(6-(3,5-dichlorophenoxy)-3-pyridinyl)urea.

92. The method of claim 47 in which the active agent is 1-(2-chloro-6-methoxybenzoyl)-3-(6-(3,5-dichlorophenoxy)-3-pyridinyl)urea.

93. The method of claim 47 in which the active agent is 1-(2-fluoro-6-methoxybenzoyl)-3-(6-(3,5-dichlorophenoxy)-3-pyridinyl)urea.

94. The method of claim 47 in which the active agent is 1-(2-chloro-6-fluorobenzoyl)-3-(6-(3,5-dichlorophenoxy)-3-pyridinyl)urea.

95. The method of claim 47 in which the active agent is 1-(2,6-dichlorobenzoyl)-3-(6-(2-chloro-5-(trifluoromethyl)phenoxy)-3-pyridinyl)urea.

96. The method of claim 47 in which the active agent is 1-(2,6-dimethoxybenzoyl)-3-(6-(2-chloro-5-(trifluoromethyl)phenoxy)-3-pyridinyl)urea.

97. The method of claim 47 in which the active agent is 1-(2,6-difluorobenzoyl)-3-(6-(2-chloro-5-(trifluoromethyl)phenoxy)-3-pyridinyl)urea.

98. The method of claim 47 in which the active agent is 1-(2-chloro-6-methoxybenzoyl)-3-(6-(2-chloro-5-(trifluoromethyl)phenoxy)-3-pyridinyl)urea.

99. The method of claim 47 in which the active agent is 1-(2-fluoro-6-methoxybenzoyl)-3-(6-(2-chloro-5-(trifluoromethyl)phenoxy)-3-pyridinyl)urea.

100. The method of claim 47 in which the active agent is 1-(2-chloro-6-fluorobenzoyl)-3-(6-(2-chloro-5-(trifluoromethyl)phenoxy)-3-pyridinyl)urea.

101. The method of claim 47 in which the active agent is 1-(2,6-dimethoxybenzoyl)-3-(6-(3-(trifluoromethyl)phenoxy)-3-pyridinyl)urea.

102. The method of claim 47 in which the active agent is 1-(2,6-difluorobenzoyl)-3-(6-(3-(trifluoromethyl)phenoxy)-3-pyridinyl)urea.

103. The method of claim 47 in which the active agent is 1-(2-chloro-6-methoxybenzoyl)-3-(6-(3-(trifluoromethyl)phenoxy)-3-pyridinyl)urea.

104. The method of claim 47 in which the active agent is 1-(2-fluoro-6-methoxybenzoyl)-3-(6-(3-(trifluoromethyl)phenoxy)-3-pyridinyl)urea.

105. The method of claim 47 in which the active agent is 1-(2-chloro-6-fluorobenzoyl)-3-(6-(3-(trifluoromethyl)phenoxy)-3-pyridinyl)urea.

106. The method of claim 47 in which the active agent is 1-(2,6-dichlorobenzoyl)-3-(6-(2,4-dichlorobenzyloxy)-3-pyridinyl)urea.

107. The method of claim 47 in which the active agent is 1-(2,6-dimethoxybenzoyl)-3-(6-(2,4-dichlorobenzyloxy)-3-pyridinyl)urea.

108. The method of claim 47 in which the active agent is 1-(2,6-difluorobenzoyl)-3-(6-(2,4-dichlorobenzyloxy)-3-pyridinyl)urea.

109. The method of claim 47 in which the active agent is 1-(2-chloro-6-methoxybenzoyl)-3-(6-(2,4-dichlorobenzyloxy)-3-pyridinyl)urea.

110. The method of claim 47 in which the active agent is 1-(2-fluoro-6-methoxybenzoyl)-3-(6-(2,4-dichlorobenzyloxy)-3-pyridinyl)urea.

111. The method of claim 47 in which the active agent is 1-(2-chloro-6-fluorobenzoyl)-3-(6-(2,4-dichlorobenzyloxy)-3-pyridinyl)urea.

112. The method of claim 47 in which the active agent is 1-(2,6-dichlorobenzoyl)-3-(6-(4-chloro-3-(trifluoromethyl)phenoxy)-3-pyridinyl)urea.

113. The method of claim 47 in which the active agent is 1-(2,6-dimethoxybenzoyl)-3-(6-(4-chloro-3-(trifluoromethyl)phenoxy)-3-pyridinyl)urea.

114. The method of claim 47 in which the active agent is 1-(2,6-difluorobenzoyl)-3-(6-(4-chloro-3-(trifluoromethyl)phenoxy)-3-pyridinyl)urea.

115. The method of claim 47 in which the active agent is 1-(2-chloro-6-methoxybenzoyl)-3-(6-(4-chloro-3-(trifluoromethyl)phenoxy)-3-pyridinyl)urea.

116. The method of claim 47 in which the active agent is 1-(2-fluoro-6-methoxybenzoyl)-3-(6-(4-chloro-3-(trifluoromethyl)phenoxy)-3-pyridinyl)urea.

117. The method of claim 47 in which the active agent is 1-(2-chloro-6-fluorobenzoyl)-3-(6-(4-chloro-3-(trifluoromethyl)phenoxy)-3-pyridinyl)urea.

118. The method of claim 47 in which the active agent is 1-(2,6-dichlorobenzoyl)-3-(5-chloro-6-(3-(trifluoromethyl)phenoxy)-3-pyridinyl)urea.

119. The method of claim 47 in which the active agent is 1-(2,6-dimethoxybenzoyl)-3-(6-(4-chlorophenoxy)-3-pyridinyl)urea.

120. The composition of claim 56 in which the active agent is 1-(2,6-dichlorobenzoyl)-3-(6-(3,5-dichlorophenoxy)-3-pyridinyl)urea.

121. The composition of claim 56 in which the active agent is 1-(2,6-difluorobenzoyl)-3-(6-(3,5-dichlorophenoxy)-3-pyridinyl)urea.

122. The composition of claim 56 in which the active agent is 1-(2-chloro-6-methoxybenzoyl)-3-(6-(3,5-dichlorophenoxy)-3-pyridinyl)urea.

123. The composition of claim 56 in which the active agent is 1-(2-fluoro-6-methoxybenzoyl)-3-(6-(3,5-dichlorophenoxy)-3-pyridinyl)urea.

124. The composition of claim 56 in which the active agent is 1-(2-chloro-6-fluorobenzoyl)-3-(6-(3,5-dichlorophenoxy)-3-pyridinyl)urea.

125. The composition of claim 56 in which the active agent is 1-(2,6-dichlorobenzoyl)-3-(6-(2-chloro-5-(trifluoromethyl)phenoxy)-3-pyridinyl)urea.

126. The composition of claim 56 in which the active agent is 1-(2,6-dimethoxybenzoyl)-3-(6-(2-chloro-5-(trifluoromethyl)phenoxy)-3-pyridinyl)urea.

127. The composition of claim 56 in which the active agent is 1-(2,6-difluorobenzoyl)-3-(6-(2-chloro-5-(trifluoromethyl)phenoxy)-3-pyridinyl)urea.

128. The composition of claim 56 in which the active agent is 1-(2-chloro-6-methoxybenzoyl)-3-(6-(2-chloro-5-(trifluoromethyl)phenoxy)-3-pyridinyl)urea.

129. The composition of claim 56 in which the active agent is 1-(2-fluoro-6-methoxybenzoyl)-3-(6-(2-chloro-5-(trifluoromethyl)phenoxy)-3-pyridinyl)urea.

130. The composition of claim 56 in which the active agent is 1-(2-chloro-6-fluorobenzoyl)-3-(6-(2-chloro-5-(trifluoromethyl)phenoxy)-3-pyridinyl)urea.

131. The composition of claim 56 in which the active agent is 1-(2,6-dimethoxybenzoyl)-3-(6-(3-trifluoromethyl)phenoxy)-3-pyridinyl)urea.

132. The composition of claim 56 in which the active agent is 1-(2,6-difluorobenzoyl)-3-(6-(3-(trifluoromethyl)phenoxy)-3-pyridinyl)urea.

133. The composition of claim 56 in which the active agent is 1-(2-chloro-6-methoxybenzoyl)-3-(6-(3-(trifluoromethyl)phenoxy)-3-pyridinyl)urea.

134. The composition of claim 56 in which the active agent is 1-(2-fluoro-6-methoxybenzoyl)-3-(6-(3-(trifluoromethyl)phenoxy)-3-pyridinyl)urea.

135. The composition of claim 56 in which the active agent is 1-(2-chloro-6-fluorobenzoyl)-3-(6-(3-(trifluoromethyl)phenoxy)-3-pyridinyl)urea.

136. The composition of claim 56 in which the active agent is 1-(2,6-dichlorobenzoyl)-3-(6-(2,4-dichlorobenzyloxy)-3-pyridinyl)urea.

137. The composition of claim 56 in which the active agent is 1-(2,6-dimethoxybenzoyl)-3-(6-(2,4-dichlorobenzyloxy)-3-pyridinyl)urea.

138. The composition of claim 56 in which the active agent is 1-(2,6-difluorobenzoyl)-3-(6-(2,4-dichlorobenzyloxy)-3-pyridinyl)urea.

139. The composition of claim 56 in which the active agent is 1-(2-chloro-6-methoxybenzoyl)-3-(6-(2,4-dichlorobenzyloxy)-3-pyridinyl)urea.

140. The composition of claim 56 in which the active agent is 1-(2-fluoro-6-methoxybenzoyl)-3-(6-(2,4-dichlorobenzyloxy)-3-pyridinyl)urea.

141. The composition of claim 56 in which the active agent is 1-(2-chloro-6-fluorobenzoyl)-3-(6-(2,4-dichlorobenzyloxy)-3-pyridinyl)urea.

142. The composition of claim 56 in which the active agent is 1-(2,6-dichlorobenzoyl)-3-(6-(4-chloro-3-(trifluoromethyl)phenoxy)-3-pyridinyl)urea.

143. The composition of claim 56 in which the active agent is 1-(2,6-dimethoxybenzoyl)-3-(6-(4-chloro-3-(trifluoromethyl)phenoxy)-3-pyridinyl)urea.

144. The composition of claim 56 in which the active agent is 1-(2,6-difluorobenzoyl)-3-(6-(4-chloro-3-(trifluoromethyl)phenoxy)-3-pyridinyl)urea.

145. The composition of claim 56 in which the active agent is 1-(2-chloro-6-methoxybenzoyl)-3-(6-(4-chloro-3-(trifluoromethyl)phenoxy-3-pyridinyl)urea.

146. The composition of claim 56 in which the active agent is 1-(2-fluoro-6-methoxybenzoyl)-3-(6-(4-chloro-3-(trifluoromethyl)phenoxy)-3-pyridinyl)urea.

147. The composition of claim 56 in which the active agent is 1-(2-chloro-6-fluorobenzoyl)-3-(6-(4-chloro-3-(trifluoromethyl)phenoxy)-3-pyridinyl)urea.

148. The composition of claim 56 in which the active agent is 1-(2,6-dichlorobenzoyl)-3-(5-chloro-6-(3-(trifluoromethyl)phenoxy)-3-pyridinyl)urea.

149. The composition of claim 56 in which the active agent is 1-(2,6-dimethoxybenzoyl)-3-(6-(4-chlorophenoxy)-3-pyridinyl)urea.

150. Compound of the formula

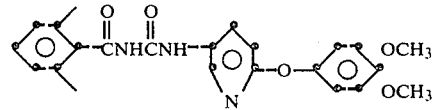

wherein each R is independently chloro, fluoro, methyl, or methoxy.

151. The compound of claim 150 which is 1-(2,6-dichlorobenzoyl)-3-(6-(3,5-dimethoxyphenoxy)-3-pyridinyl)urea.

152. The compound of claim 150 which is 1-(2,6-dimethoxybenzoyl)-3-(6-(3,5-dimethoxyphenoxy)-3-pyridinyl)urea.

153. The compound of claim 150 which is 1-(2,6-difluorobenzoyl)-3-(6-(3,5-dimethoxyphenoxy)-3-pyridinyl)urea.

154. The compound of claim 150 which is 1-(2-chloro-6-methoxybenzoyl)-3-(6-(3,5-dimethoxyphenoxy)-3-pyridinyl)urea.

155. The compound of claim 150 which is 1-(2-fluoro-6-methoxybenzoyl)-3-(6-(3,5-dimethoxyphenoxy)-3-pyridinyl)urea.

156. The compound of claim 150 which is 1-(2-chloro-6-fluorobenzoyl)-3-(6-(3,5-dimethoxyphenoxy)-3-pyridinylurea.

157. Method of suppressing insects of an order selected from the group consisting of Coleoptera, Diptera, Lepidoptera, and Orthoptera, which comprises applying to the locus of the insects an effective amount of an active agent which is a compound of claim 150.

158. The method of claim 157 in which the active agent is 1-(2,6-dichlorobenzoyl)-3-(6-(3,5-dimethoxyphenoxy)-3-pyridinyl)urea.

159. Composition comprising a surface active agent and an insecticidally effective amount of an active agent which is a compound of claim 150.

160. The composition of claim 159 in which the active agent is 1-(2,6-dichlorobenzoyl)-3-(6-(3,5-dimethoxyphenoxy)-3-pyridinyl)urea.

* * * * *

UNITED STATES PATENT AND TRADEMARK OFFICE
CERTIFICATE OF CORRECTION

PATENT NO. : 4,264,605

DATED : April 28, 1981

INVENTOR(S) : Robert G. Suhr and John L. Miesel

It is certified that error appears in the above-identified patent and that said Letters Patent are hereby corrected as shown below:

Column 1, line 38, "$R^2$ is" should read --$R^3$ is--.

Column 2, lines 22-27,

" 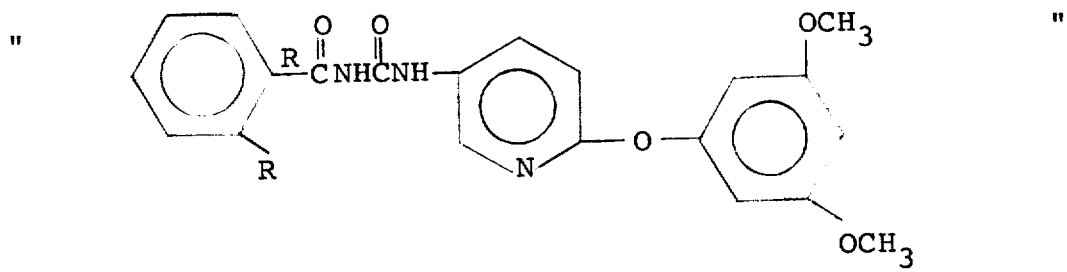 "

should read

-- 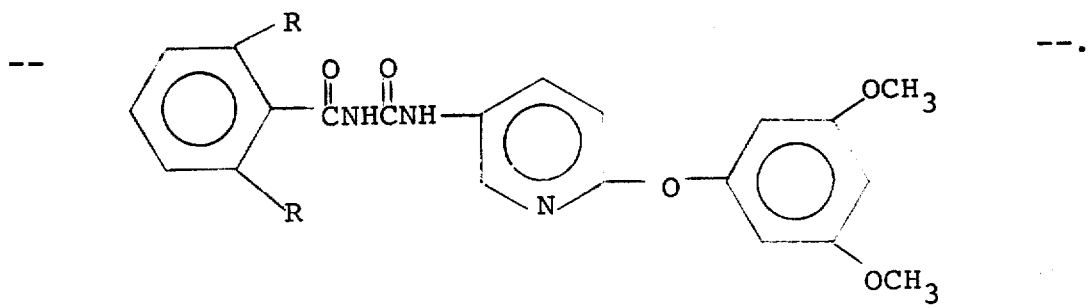 --.

UNITED STATES PATENT AND TRADEMARK OFFICE
CERTIFICATE OF CORRECTION

PATENT NO. : 4,264,605
DATED : April 28, 1981
INVENTOR(S) : Robert G. Suhr and John L. Miesel It is certified that error appears in the above–identified patent and that said Letters Patent are hereby corrected as shown below:

Column 3, line 66, "Battowski," should read --Batkowski,--.

Column 5, line 10, "(3,5-DIMETHYLPHENOXY)-NITROPYRIDINE" should read --(3,5-DIMETHYLPHENOXY)-3-NITROPYRIDINE--.

Column 6, lines 51-52, "Calc. for $C_{19}H_{12}Cl_2N_3O_2S$: C, 50.41; H, 2.67; N, 9.28. Found: C, 50.54; H, 2.97; N, 9.45." should be deleted.

Column 17, example 218, "3-(6-2,4-dichlorobenzyloxy)" should read --3-(6-(2,4-dichlorobenzyloxy)--.

Column 21, line 55, "and web-" should read --sod web- --.

Column 31, Example No. 74, under "4 days Column", "0" should read --7--.

Column 36, line 64, "$R^2$ is" should read --$R^3$ is--.

UNITED STATES PATENT AND TRADEMARK OFFICE
CERTIFICATE OF CORRECTION

PATENT NO. : 4,264,605
DATED : April 28, 1981
INVENTOR(S) : Robert G. Suhr and John L. Miesel It is certified that error appears in the above-identified patent and that said Letters Patent are hereby corrected as shown below:

Column 44, lines 45-50,

" 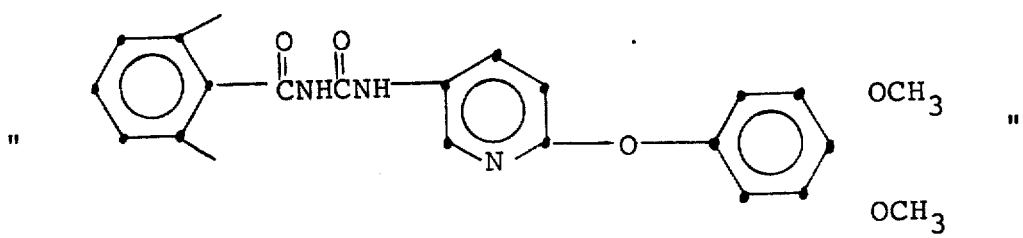 "

should read

-- 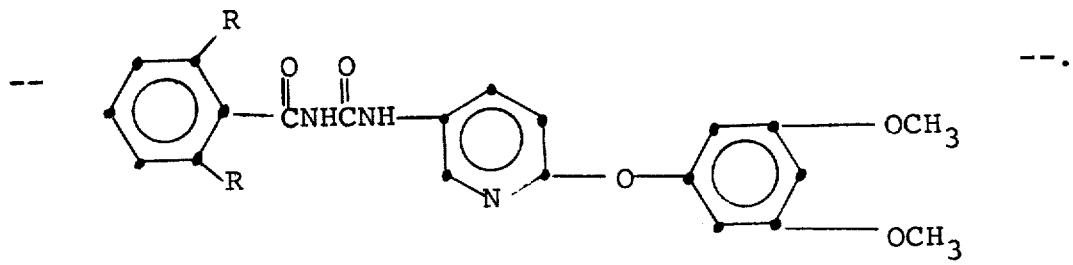 --.

Signed and Sealed this

Twenty-ninth Day of December 1981

[SEAL]

Attest:

GERALD J. MOSSINGHOFF

Attesting Officer    Commissioner of Patents and Trademarks